(12) United States Patent
Magda et al.

(10) Patent No.: US 7,160,873 B2
(45) Date of Patent: Jan. 9, 2007

(54) TEXAPHYRIN COORDINATION COMPOUNDS AND USES THEREOF

(75) Inventors: Darren Magda, Cupertino, CA (US); Dale Miles, Sunnyvale, CA (US); Nikolay Gerasimchuk, Springfield, MO (US); Cheryl Lepp, Mountain View, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 87 days.

(21) Appl. No.: 11/033,431

(22) Filed: Jan. 7, 2005

(65) Prior Publication Data

US 2005/0159401 A1 Jul. 21, 2005

Related U.S. Application Data

(62) Division of application No. 10/415,916, filed as application No. PCT/US01/43590 on Nov. 16, 2001, now Pat. No. 6,919,327.

(60) Provisional application No. 60/249,523, filed on Nov. 17, 2000.

(51) Int. Cl.
*A61K 7/407* (2006.01)
*A61K 31/555* (2006.01)
*C07D 487/22* (2006.01)

(52) U.S. Cl. .................. 514/185; 514/410; 534/11; 534/15; 540/145; 540/465; 540/472

(58) Field of Classification Search ................ 514/185, 514/410; 534/11, 15; 540/145, 465, 472
See application file for complete search history.

(56) References Cited

U.S. PATENT DOCUMENTS 5,457,183 A * 10/1995 Sessler et al. ................ 534/11

\* cited by examiner

*Primary Examiner*—Peter O'Sullivan
(74) *Attorney, Agent, or Firm*—Wilson, Sonsini, Goodrich & Rosati

(57) ABSTRACT

Novel coordination polymers, their pharmaceutical formulations, useful for treating atheroma, tumors and other neoplastic tissue, as well as other conditions that are responsive to the induction of targeted oxidative stress, are disclosed.

8 Claims, 5 Drawing Sheets

TEXAPHYRIN COORDINATION COMPOUNDS AND USES THEREOF

CROSS-REFERENCES TO RELATED APPLICATIONS

This application is a divisional of U.S. patent application Ser. No. 10/415,916, filed Nov. 16, 2001, allowed on Jul. 19, 2005 now U.S. Pat. No. 6,919,327, of which the said application is the National Stage of International Application No. PCT/US01/43590, filed Nov. 16, 2001, published in English under PCT Article 21(2) as Publication No. WO 02/39953, on May 23, 2002, which claimed the benefit of priority from U.S. Provisional Application No. 60/249,523, filed Nov. 17, 2000, all of which are incorporated herein by reference.

BACKGROUND OF THE INVENTION

1. Field of the Invention

This invention relates to novel compounds and their pharmaceutical formulations, and their uses to treat atheroma, tumors and other neoplastic tissue, as well as other conditions that are responsive to the induction of targeted oxidative stress.

2. Background Information

Treatment of solid mammalian tumors with ionizing radiation involves the in situ generation of hydroxyl radicals and other reactive oxygen species that, due to the focusability of the ionizing radiation are primarily located in the tumor, i.e., in tumor cells. These reactive species possess extreme oxidizing properties which oxidize biomolecules in vivo thereby interfering with cellular metabolism, as discussed by Buettner, et al., Radiation Research, *Catalytic Metals, Ascorbate and Free Radicals: Combinations to Avoid*, 145:532–541 (1996).

Tumor treatment via the use of ionizing radiation can be enhanced by increasing the radio sensitivity of the tumor cells. One method suggested for enhancing radio sensitivity has been the external administration of a compound having a high affinity for electrons, which ideally localizes in the tumor. Proposed radiation sensitizers include compounds such as halogenated pyrimidines, nitroimidazoles and gadolinium (III) complexes of the pentadentate macrocycle Texaphyrin, as described by Sessler, et al., J. Phys. Chem. A, *One-Electron Reduction and Oxidation Studies of the Radiations Sensitizer Gadolinium (III) Texaphyrin (PCI-120) and Other Water Soluble Metallotexaphyrins*, 103: 787–794 (1999).

Texaphyrins are known to be useful as radiation sensitizers, and also for the treatment of plaque caused by atherosclerosis, retinal diseases, for the destruction of retroviruses, especially HIV and the like.

Efficacy of texaphyrins is dependent on its ability to penetrate cellular membranes and thereby increase its intracellular concentration. Thus intracellular availability of texaphyrin is a key to its biological activity and effectiveness. Texaphyrins are known to penetrate cell membranes and are known to have an effective intracellular concentration to have beneficial biological activity. An improvement in the ability of a drug substance to enter cellular membranes is however always welcome. It has been surprisingly discovered that premixing texaphyrins with an oxalate salt or an oxalate precursor, for example ascorbic acid, gives rise to a compound whose structure differs from that of a Texaphyrin, but is seen to accumulate more rapidly in tumor cells, plaque, etc.

SUMMARY OF THE INVENTION

This invention relates to a method of treating tumors and other neoplastic tissue, plaque caused by atherosclerosis, viruses, including HIV, and retinal diseases using the polymeric complex of the present invention.

The present invention also relates to polymeric complexes formed by treating texaphyrins with oxalate salts or oxalate precursors and their pharmaceutical compositions.

The present invention thus provides a method for treating a disease or condition in a mammal resulting from the presence of neoplastic tissue, neovascularization, or an atheroma, said method comprising:

(a) administering to a mammal in need of such treatment a therapeutically effective amount of a coordination polymer comprising structural units "A":

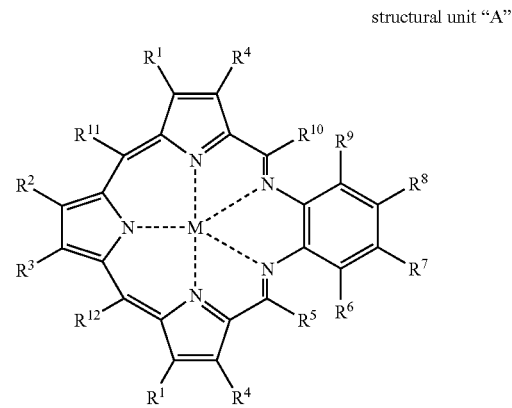

structural unit "A"

wherein:

M is a trivalent metal cation;

$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl, and structural unit "B"

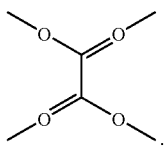

Another aspect of the present invention provides a coordination polymer comprising structural units "A":

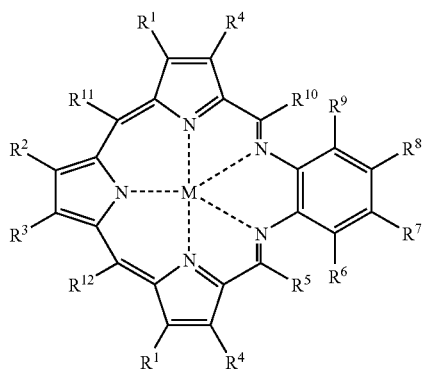

wherein:

M is a trivalent metal cation;

$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl, and structural unit "B"

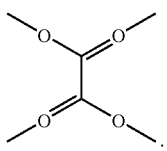

Provided in yet another aspect is a coordination polymer wherein structural unit "A" is represented by

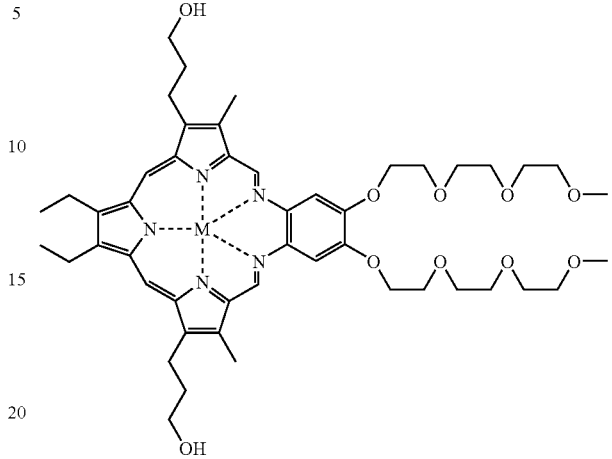

wherein

M independently at each occurrence represents Gd(III) or Lu(III); and structural unit "B" is represented by

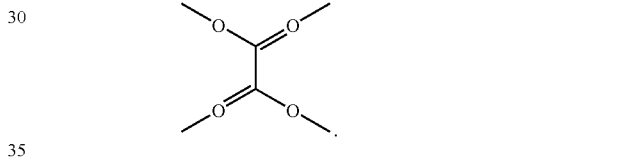

Yet another aspect provides a process of making a coordination polymer comprising structural units "A":

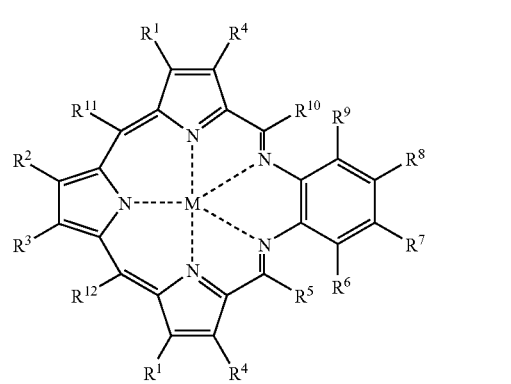

wherein:

M is a trivalent metal cation;

AL is an apical ligand;

n is an integer of 1–5;

$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$; and $R^{12}$ are independently hydrogen, optionally substituted alkyl, optionally substituted aryl, optionally substituted alkoxy, optionally substituted carboxyalkyl, or optionally substituted carboxyamidealkyl; and structural unit "B"

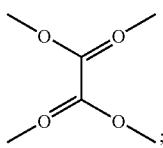

structural unit "B"

said process comprising contacting a compound of Formula A

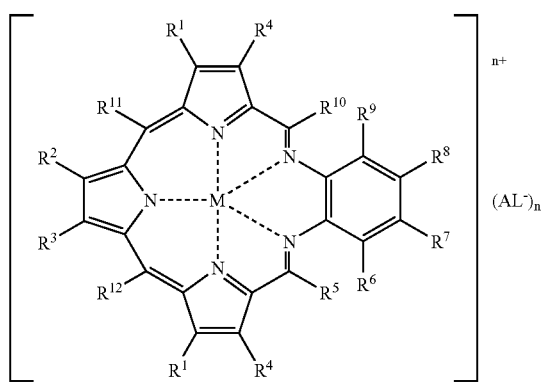

Formula A wherein
M is a trivalent metal cation;
AL is an apical ligand;
n is an integer of 1–5;
$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl;

with an oxalate salt or an oxalate precursor, to form a coordination polymer comprising structural units "A" and "B".

Also provided is a coordination polymer prepared by contacting a compound of Formula A

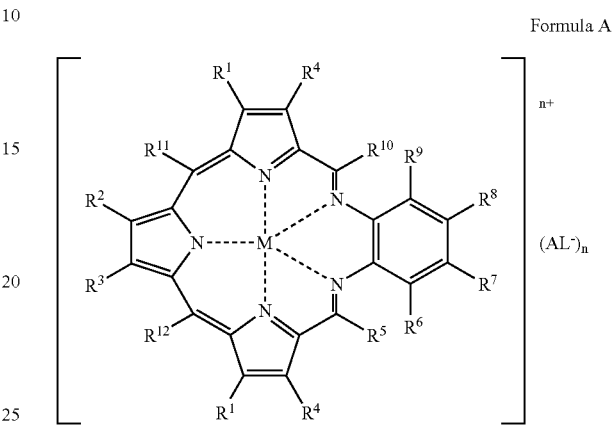

Formula A wherein:
M is a trivalent metal cation;
AL is an apical ligand;
n is an integer of 1–5;
$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, option ally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl;

with an oxalate salt or an oxalate precursor, optionally in the presence of oxygen.

DETAILED DESCRIPTION OF THE INVENTION

Figure 1:
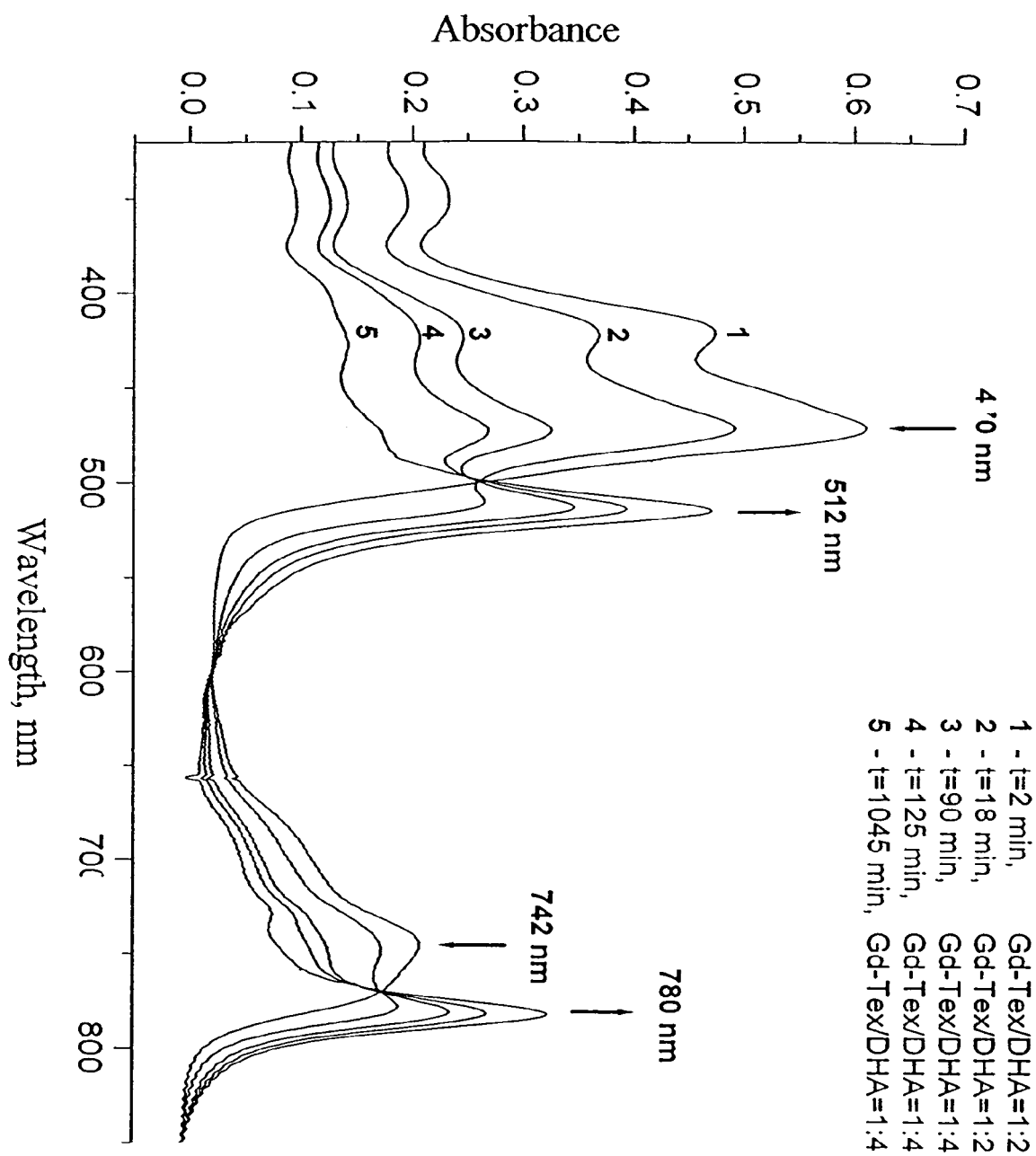
FIG. 1 depicts the time course showing changes in optical spectra occurring upon incubation of Motexafin Gadolinium (GdTex) with dihydroascorbate (DHA) in a buffer (see Example 2).
Figure 2:
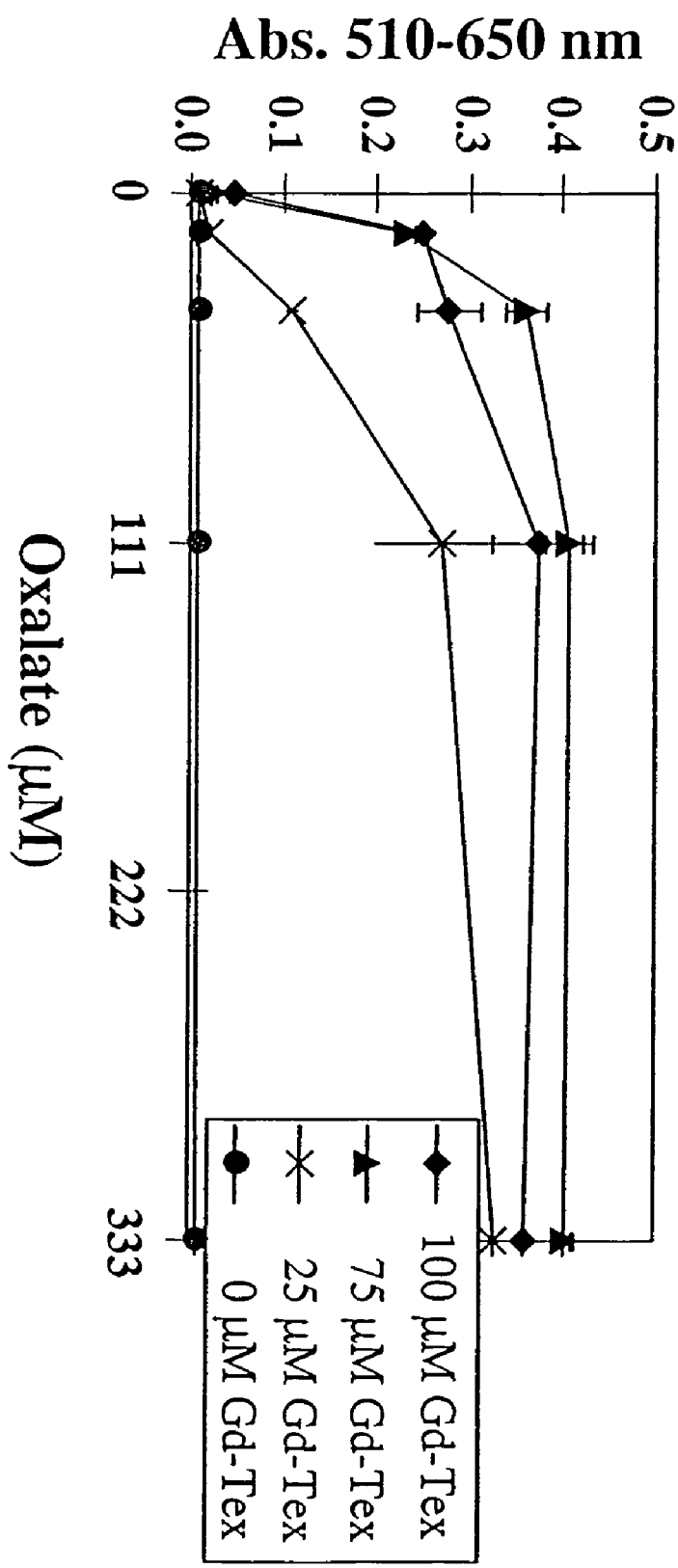
FIG. 2 refers to cellular uptake of GdTex oxalate complex as measured by absorbance (see Example 7).
Figure 3:
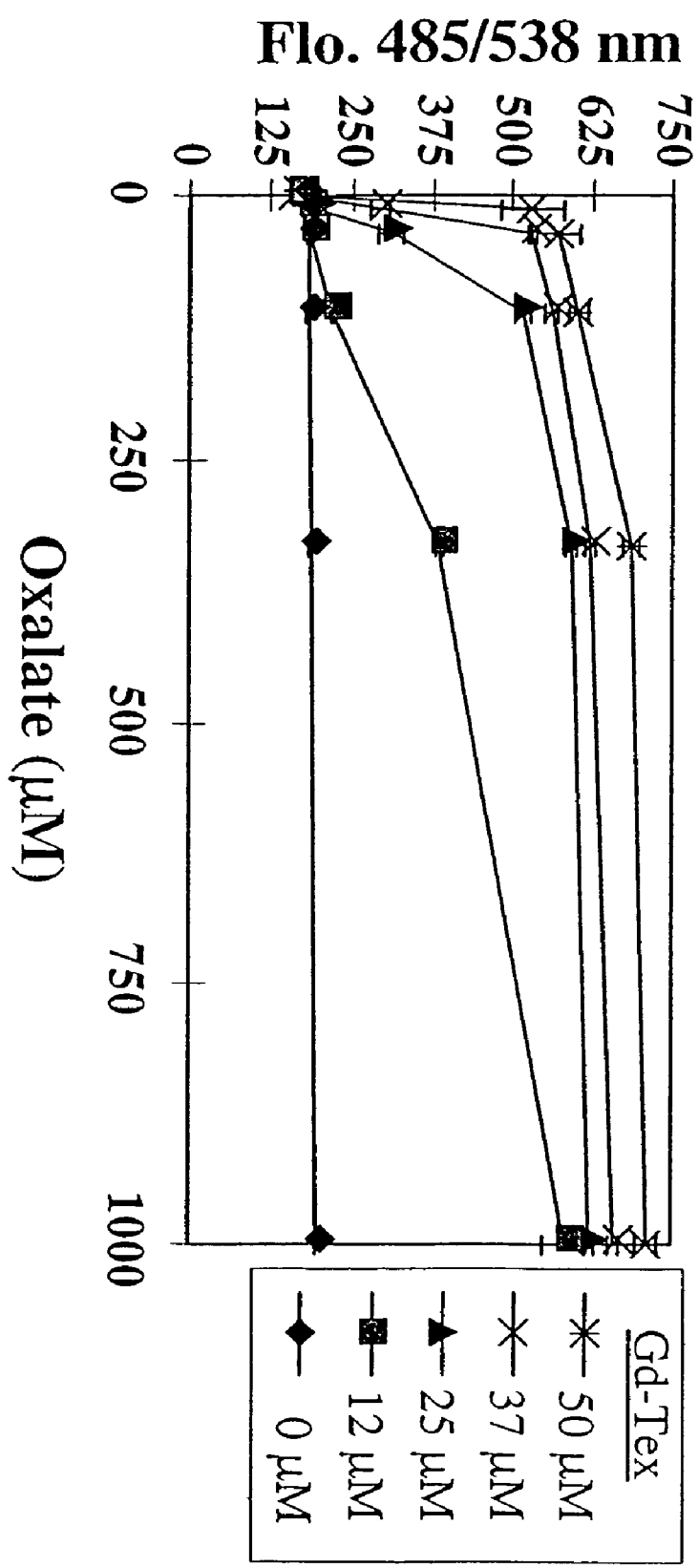
FIG. 3 refers to cellular uptake of GdTex oxalate complex as measured by dichlorofluoroscin acetate (DCFA) oxidation to form dichlorofluoresin (DCF) (see Example 7).

The present invention thus provides a method for treating a disease or condition in a mammal resulting from the presence of neoplastic tissue, neovascularization, or an atheroma, said method comprising:

(a) administering to a mammal in need of such treatment a therapeutically effective amount of a coordination polymer comprising structural units "A":

structural unit "A"

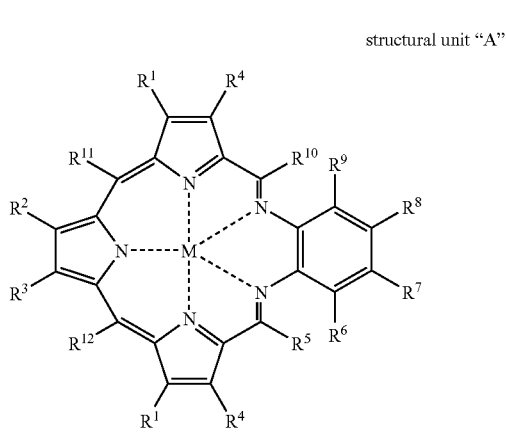

wherein:
M is a trivalent metal cation;
$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl, and structural unit "B"

structural unit "B"

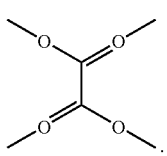

A preferred embodiment provides a method wherein within structural unit "A"

M independently at each occurrence represents Gd(III), Lu(III), Eu(III), Tb(III), Dy(III), Ho(III), Er(III), Tm(III), Yb(III), or Y(III);
$R^1$ represents $(CH_2)_{2-4}$—OH;
$R^2$ and $R^3$ independently represent $C_1$–$C_3$-alkyl;
$R^4$ represents ethyl, methyl or propyl;
$R^5$, $R^6$, $R^9$, $R^{10}$, $R^{11}$ and $R^{12}$ independently represent H or methyl; and
$R^7$ and $R^8$ represent O—[$(CH_2)_2O]_3$—$C_{1-2}$-alkyl or O—$(CH_2)_{2-4}$OH.

A further preferred embodiment provides a method of Claim 2 wherein structural unit "A" is represented by

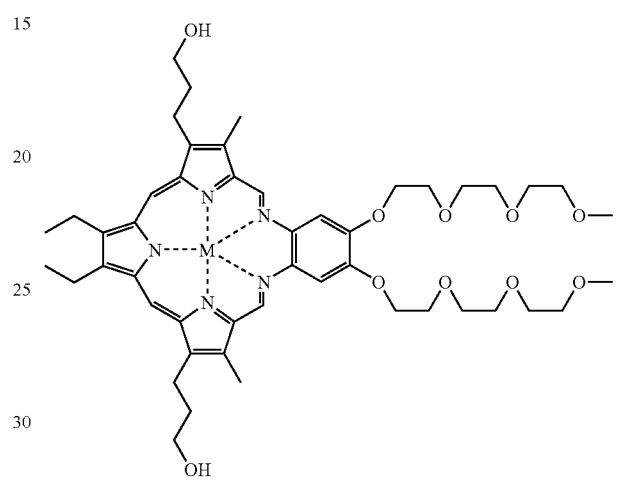

wherein,
M independently at each occurrence represents Gd(III), Lu(III), Eu(III), Tb(III), Dy(III), Ho(III), Er(III), Tm(III), Yb(III), or Y(III).

Another preferred embodiment provides a method wherein said method further comprises treating the area in proximity to the neoplastic tissue with a therapeutic energy means or with a chemotherapeutic agent, or treating the area in proximity to the neovascularization or atheroma with a therapeutic energy means; and wherein the optional therapeutic energy means is chosen from photoirradiation, ionizing radiation, neutron irradiation, and ultrasound.

Another aspect of the present invention provides a coordination polymer comprising structural units "A":

structural unit "A"

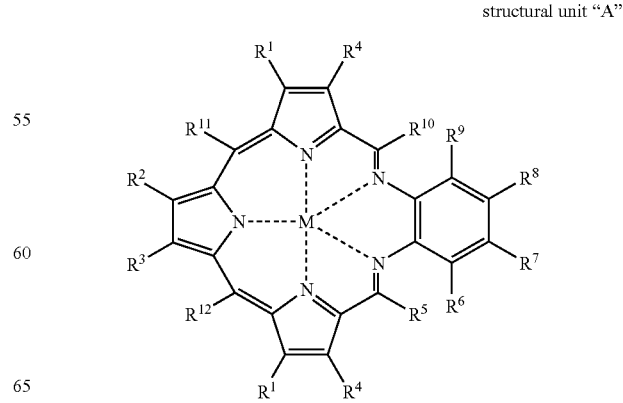

wherein:

M is a trivalent metal cation;

$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl, and structural unit "B"

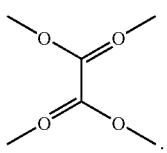

structural unit "B"

A preferred coordination polymer is one wherein within structural unit "A", M independently at each occurrence represents Gd(III), Lu(III), Eu(III), Tb(III), Dy(III), Ho(III), Er(III), Tm(III), Yb(III), or Y(III);

$R^1$ represents $(CH_2)_{2-4}$—OH;

$R^2$ and $R^3$ independently represent $C_1$–$C_3$-alkyl;

$R^4$ represents ethyl, methyl or propyl;

$R^5$, $R^6$, $R^9$, $R^{10}$, $R^{11}$ and $R^{12}$ independently represent H or methyl; and $R^7$ and $R^8$ represent O—$[(CH_2)_2O]_3$—$C_{1-2}$-alkyl or O—$(CH_2)_{2-4}$OH.

A further preferred coordination polymer comprises structural unit "A" represented by

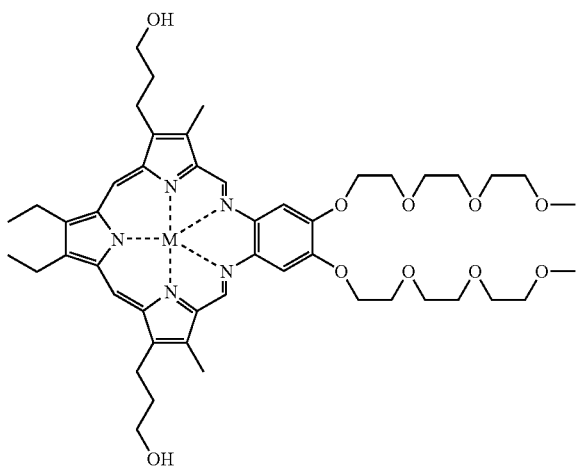

wherein

M independently at each occurrence represents Gd(III), Lu(III), Eu(III), Tb(III), Dy(III), Ho(III), Er(III), Tm(III), Yb(III), or Y(III).

A particularly preferred coordination polymer comprises a structural unit "A" is represented by

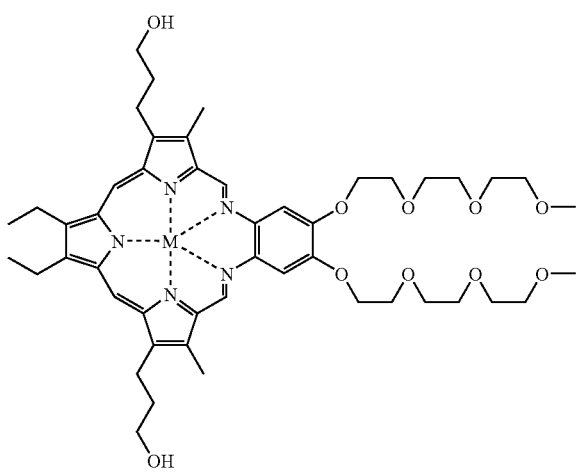

wherein

M independently at each occurrence represents Gd(III) or Lu(III); and structural unit "B" is represented by

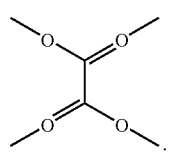

structural unit "B"

Another particularly preferred coordination polymer comprises a structural unit "A" represented by

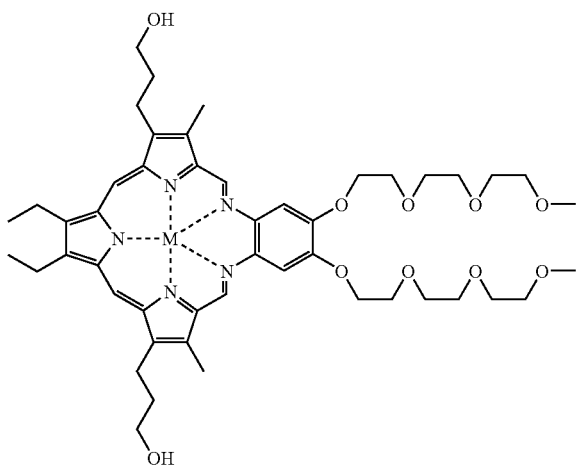

wherein
M represents Gd(III); and structural unit "B" is represented by

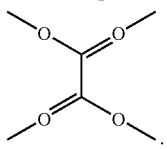
structural unit "B"

Yet another particularly preferred coordination polymer comprises structural unit "A" represented by

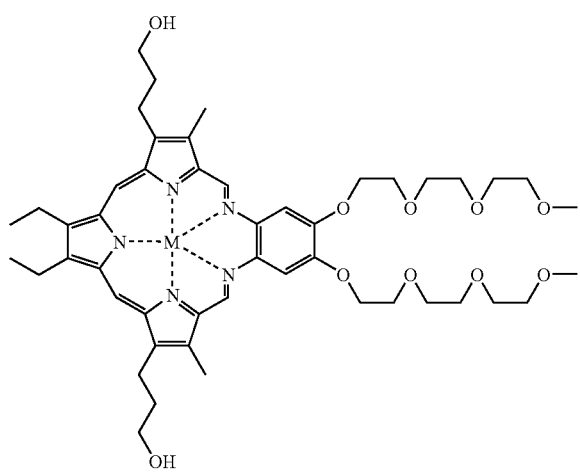

wherein
M represents Lu(III); and structural unit "B" is represented by

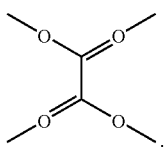
structural unit "B"

Another aspect of the present invention provides a process of making a coordination polymer comprising structural units "A":

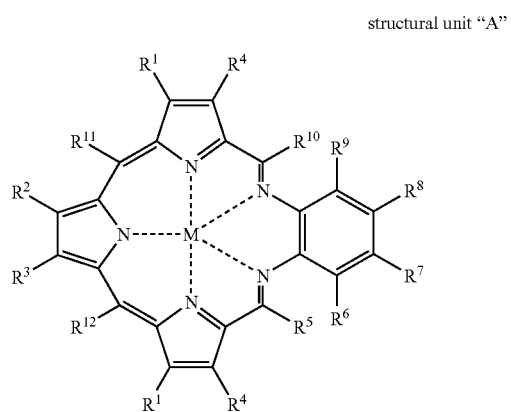
structural unit "A"

wherein:
M is a trivalent metal cation;
AL is an apical ligand;
n is an integer of 1–5;
$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and
$R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl; and structural unit "B"

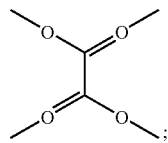
structural unit "B"

said process comprising contacting a compound of Formula A

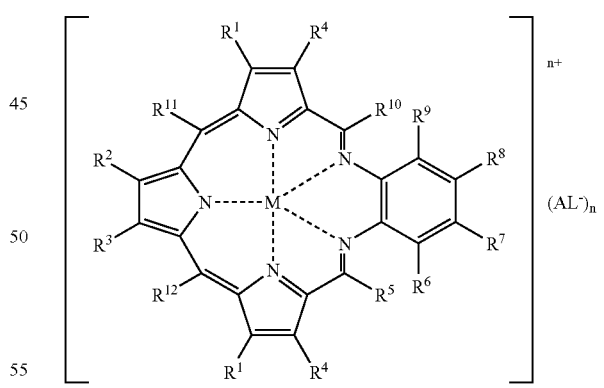
Formula A wherein
M is a trivalent metal cation;
AL is an apical ligand;
n is an integer of 1–5;
$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl;

with an oxalate salt or an oxalate precursor, to form a coordination polymer comprising structural units "A" and "B".

A preferred process is one wherein within structural unit "A"

M independently at each occurrence represents Gd(III), Lu(III), Eu(III), Tb(III), Dy(III), Ho(III), Er(III), Tm(III), Yb(III), or Y(III);

$R^1$ represents $(CH_2)_{2-4}$—OH;

$R^2$ and $R^3$ independently represent $C_1$–$C_3$-alkyl;

$R^4$ represents ethyl, methyl or propyl;

$R^5$, $R^6$, $R^9$, $R^{10}$, $R^{11}$ and $R^{12}$ independently represent H or methyl; and $R^7$ and $R^8$ represent O—$[(CH_2)_2O]_3$—$C_{1-2}$-alkyl or O—$(CH_2)_{2-4}$OH.

A further preferred process is one wherein structural unit "A" is represented by

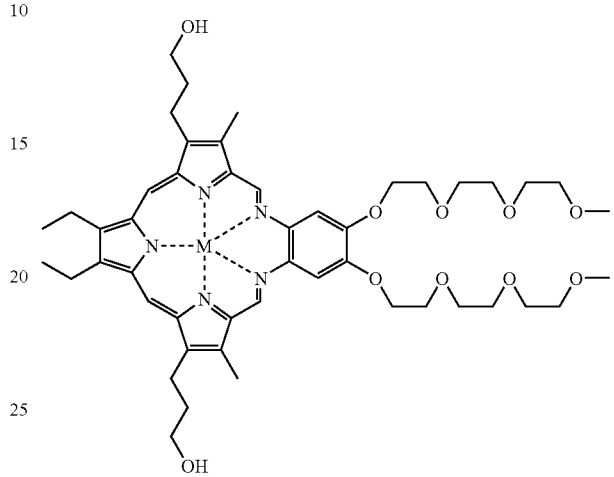

and compound of Formula A are represented by

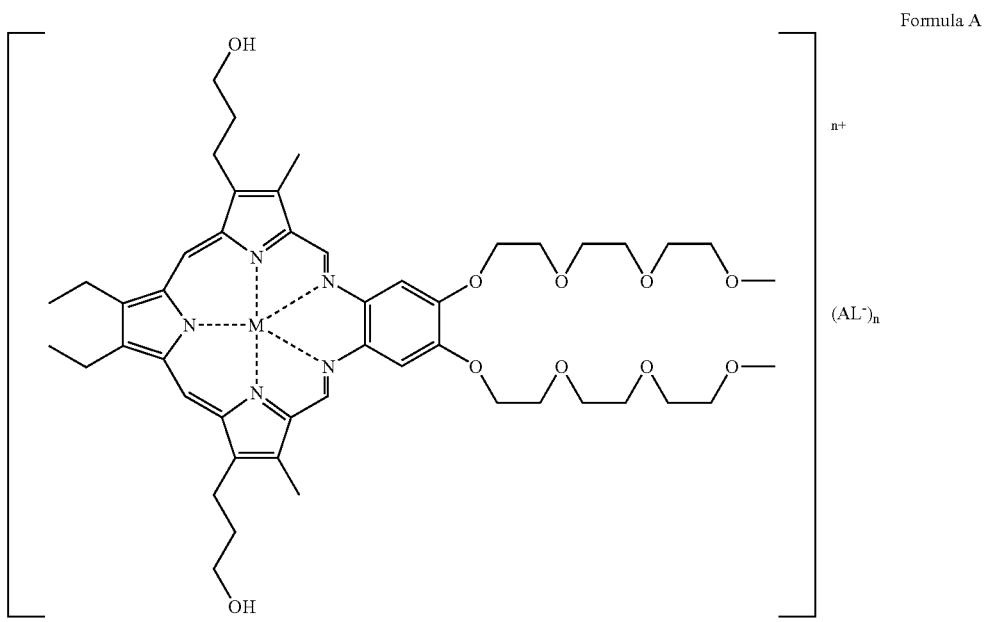

Formula A wherein

M independently at each occurrence represents Gd(III), Lu(III), Eu(III), Tb(III), Dy(III), Ho(III), Er(III), Tm(III), Yb(III), or Y(III); the process is carried out at ambient temperature and neutral pH; the oxalate or oxalate precursor is selected from ascorbate, dehydroascorbate, glyoxal and glyoxylate; and the process is carried out in the presence of oxygen.

Yet another aspect of the present invention provides a coordination polymer prepared by contacting a compound of Formula A

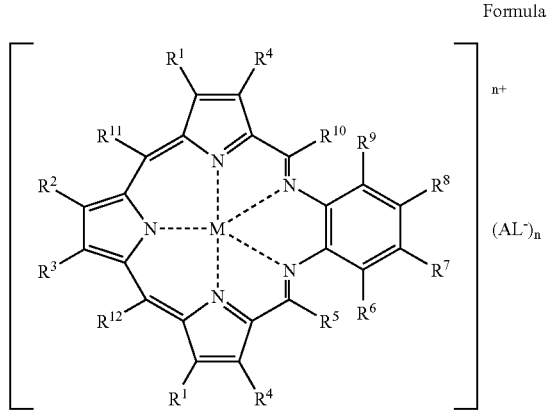

Formula A wherein:
M is a trivalent metal cation;
AL is an apical ligand;

n is an integer of 1–5;
$R^1$, $R^2$, $R^3$, $R^4$, $R^6$, $R^7$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and $R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl;

with an oxalate salt or an oxalate precursor, optionally in the presence of oxygen.

A preferred coordination polymer is one wherein within structural unit "A"

M independently at each occurrence represents Gd(III), Lu(III), Eu(III), Tb(III), Dy(III), Ho(III), Er(III), Tm(III), Yb(III), or Y(III);

$R^1$ represents $(CH_2)_{2-4}$—OH;

$R^2$ and $R^3$ independently represent $C_1$–$C_3$-alkyl;

$R^4$ represents ethyl, methyl or propyl;

$R^5$, $R^6$, $R^9$, $R^{10}$, $R^{11}$ and $R^{12}$ independently represent H or methyl; and $R^7$ and $R^8$ represent O—$[(CH_2)_2O]_3$—$C_{1-2}$-alkyl or O—$(CH_2)_{2-4}$OH; and wherein the oxalate precursor is selected from ascorbate, dehydroascorbate, glyoxal, glyoxalate, oxamate, dimethyloxalate, and oxamide.

Yet another preferred method is one wherein the compound of Formula A is represented by

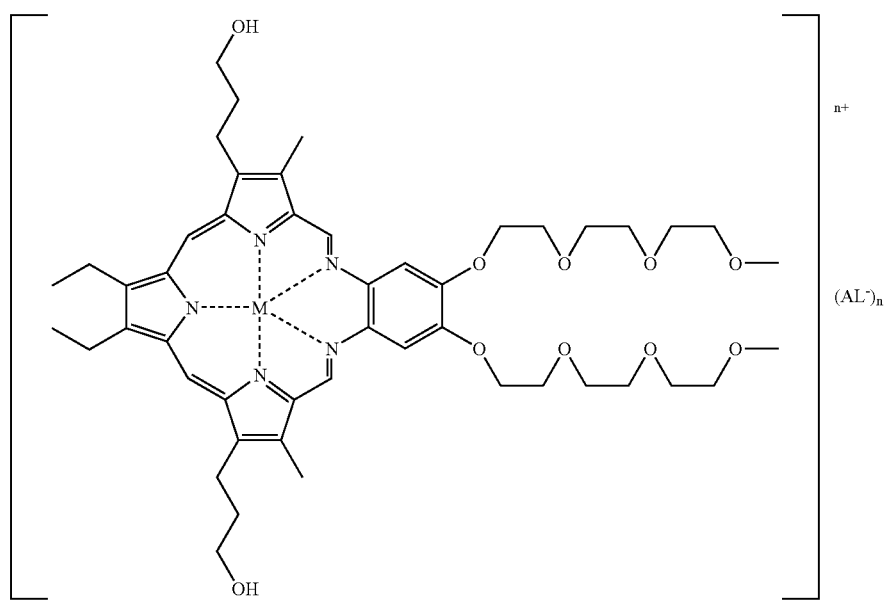

wherein

M independently at each occurrence represents Gd(III), Lu(III), Eu(III), Tb(III), Dy(III), Ho(III), Er(III), Tm(III), Yb(III), or Y(III); and n represents an integer from 1 to 3.

A particularly preferred process is one wherein the disease or condition in a mammal resulting from the presence of atheroma is atherosclerotic inflammation.

Another embodiment of the present invention provides a method for treating atherosclerotic inflammation in a mammal, said method comprising administering to the mammal:

(a) a reducing agent; and
(b) a compound of Formula I

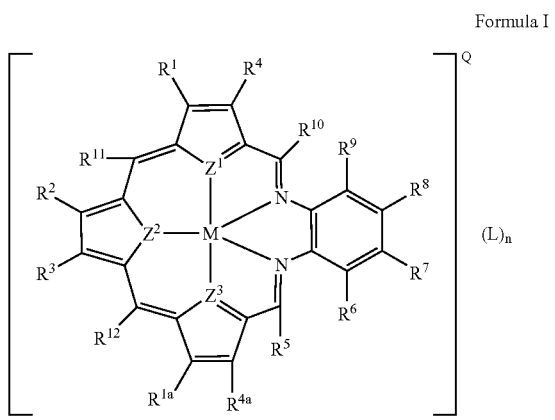

Formula I its hydrate, pharmaceutically acceptable salt or prodrug form thereof, wherein:

M represents H or a metal cation;

Q represents an integer of from about −5 to about +5;

L represents a charge balancing species;

n represents an integer of from 0 to +5;

$Z^1$, $Z^2$ and $Z^3$ independently represent N, O, CH or S;

$R^1$, $R^{1a}$, $R^2$, $R^3$, $R^4$, $R^{4a}$, $R^7$, and $R^8$ are independently selected from acyl, acyloxy, optionally substituted alkenyl, optionally substituted alkoxy, optionally substituted alkyl, optionally substituted alkynyl, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydrogen, hydroxyl, nitro, optionally substituted azo, S—$R^{31}$, SO—$R^{31}$, $SO_2$—$R^{31}$, and the moiety X—Y;

$R^6$ and $R^9$ are independently selected from acyl, acyloxy, optionally substituted alkenyl, optionally substituted alkoxy, optionally substituted alkyl, optionally substituted alkynyl, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, optionally substituted cycloalkenyl, fluoro, chloro, bromo, optionally substituted heteroaryl, optionally substituted heteroaryloxy, optionally substituted heterocyclyl, optionally substituted heterocyclooxy, hydrogen, hydroxyl, nitro, optionally substituted azo, sulfanyl, sulfinyl, sulfonyl, and the moiety X—Y;

$R^5$, $R^{10}$, $R^{11}$ and $R^{12}$ are independently selected from acyl, optionally substituted alkoxy, optionally substituted alkyl, optionally substituted aryl, halo, hydrogen, hydroxy, optionally substituted cycloalkyl, optionally substituted cycloalkenyl, optionally substituted heteroaryl, and optionally substituted heterocyclyl;

X is a covalent bond or a linker;

Y is a catalytic group, a chemotherapeutic agent or a site-directing group;

$R^{31}$ represents acyl, optionally substituted alkenyl, optionally substituted alkyl, optionally substituted alkoxy, optionally substituted alkoxycarbonyl, optionally substituted alkynyl, optionally substituted aminocarbonyl, optionally substituted aryl, carboxy, optionally substituted cycloalkyl, optionally substituted heteroaryl, or optionally substituted heterocyclyl.

A further preferred method of this embodiment is one wherein the atherosclerotic inflammation is in the form of plaque in an artery; the compound of Formula I is represented by

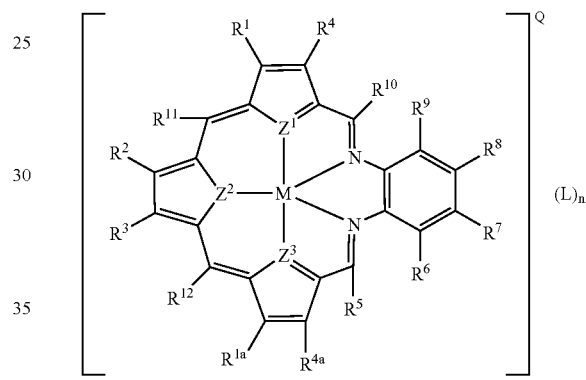

its hydrate, pharmaceutically acceptable salt or prodrug form thereof, wherein:

M represents a metal cation selected from Gd(III) and Lu(III);

Q represents an integer of 2;

L represents a charge balancing species selected from OAc, $NO_2$, Cl, and $PO_4$;

n represents an integer of 2;

$Z^1$, $Z^2$ and $Z^3$ independently represent N;

$R^1$ and $R^{1a}$ independently represent $(CH_2)_3OH$;

$R^2$ and $R^3$ independently represent $C_2H_5$;

$R^4$ and $R^{4a}$ independently represent $CH_3$;

$R^7$ and $R^8$ independently represent O—$(CH_2$—$CH_2$—$O)_3$—$CH_3$; and $R^5$, $R^6$, $R^9$, $R^{10}$, $R^{11}$ and $R^{12}$ independently represent H; and wherein the plaque is vulnerable plaque and is essentially present along walls of an artery.

A particularly preferred method is one wherein the vulnerable plaque has lipids and is inflamed; and wherein the coordination polymer is formed within a mammal by first administering to a mammal a compound of structural unit A followed by an oxalate or oxalate precursor selected from ascorbate, dehydroascorbate, glyoxal and glyoxylate.

Yet another embodiment provides a process wherein the reducing agent and the compound of Formula I

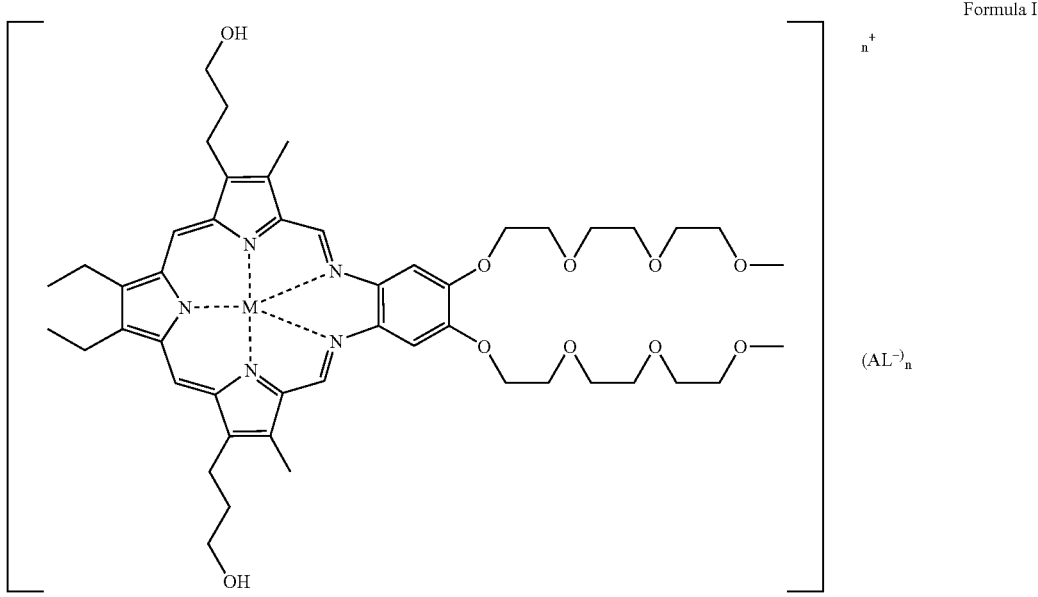

Formula I wherein
M independently at each occurrence represents Gd(III), Lu(III), Eu(III), Tb(III), Dy(III), Ho(III), Er(III), Tm(III), Yb(III), or Y(III); and
n represents an integer from 1 to 3;

are intravenously administered to the host.

A further preferred method is one wherein the reducing agent is administered at least about 30 minutes before administering a compound of Formula I. Another preferred method provides a process wherein the reducing agent and a compound of Formula I are administered simultaneously to the host. Yet another preferred embodiment provides a method wherein the host is administered a mixture of the reducing agent and a compound of Formula I. In yet another preferred embodiment is provided a method wherein the host is administered the reducing agent after the administration of a compound of Formula I.

It has now been discovered that mixing the texaphyrins with a reducing chemical entity selected from ascorbic acid, dehydroascorbate, dihydrolipoate, NADH, folate, glyoxal, glyoxalate, oxamate, dimethyloxalate, oxamide, NADPH, glutathione, nacetylcystein, pyruvate, and the like, forms a complex comprising texaphyrin and oxalate. These complexes have a characteristic UV absorption at 510 nm and 780 nm, which differ from that of the starting compound(s).

It has now been discovered that mixing the texaphyrins with a chemical entity selected from an oxalate, ascorbate, dehydroascorbate, glyoxylate, dimethyl oxalate, and the like, forms a complex comprising Texaphyrin and oxalate. These complexes have a characteristic UV absorptions at 510 nm and 780 nm, which differ from that of the starting compound(s).

This coordination complex, upon administration by injection, improves localization of the texaphyrin at the desired site (tumor, plaque, etc.) as compared to the previously known method of injecting texaphyrin alone, and thereby provides a more effective method of treatment.

As used herein, the following terms have the meanings as defined below.

The term "texaphyrin" refers to metal complexes of aromatic pentadentate macrocyclic "expanded porphyrins" which are considered as being an aromatic benzannulene containing both 18 π and 22 π-electron delocalization pathways. Such texaphyrins and their synthesis have been described, for example, by Sessler, et al., in U.S. Pat. No. 5,457,183; Sessler, et al., Accounts of Chem. Res., *Texaphyrins: Synthesis and Applications,* 27:43–50 (1994) and Hemmi, et al., U.S. Pat. No. 5,599,928 and are incorporated herein by reference.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acyl amino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxylamine, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkylene" refers to a diradical of a branched or unbranched saturated hydrocarbon chain, preferably having from 2 to 6 carbon atoms, more preferably 2 to 4 carbon atoms. This term is exemplified by groups such as ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxylamine, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkoxy" refers to the groups alkyl-O—, alkenyl-O—, cycloalkyl-O— and cycloalkenyl-O—, where alkyl, alkenyl, cycloalkyl, and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O— and substituted cycloalkenyl-O—, where substituted alkyl, substituted alkenyl, substituted cycloalkyl, and substituted cycloalkenyl are as defined herein. A preferred class of substituted alkoxy are polyoxyalkylene groups represented by the formula —O(R'O)$_q$R" where R' is an alkylene group or a substituted alkylene group, R" is selected from the group consisting of hydrogen, alkyl or substituted alkyl and q is an integer from 1 to 10. Preferably, in such groups, q is from 1 to 5 and most preferably 3.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH═CH$_2$), n-propenyl (—CH$_2$CH═CH$_2$), iso-propenyl (—C(CH$_3$)═CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxylamine, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused)rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, cycloalkyl, cycloalkenyl, substituted alkyl, substituted alkoxy, substituted alkenyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, aryl, heteroaryl and heterocyclic provided that both R's are not hydrogen.

The term "carboxyalkyl" refers to the groups "—C(O)O-alkyl", "—C(O)O-substituted alkyl", "—C(O)O-cycloalkyl", "—C(O)O-substituted cycloalkyl", "—C(O)O-alkenyl", and "—C(O)O-substituted alkenyl", where alkyl, substituted alkyl, cycloalkyl, substituted cycloalkyl, alkenyl, and substituted alkenyl, are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxylamine, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxylamine, alkoxyamino, nitro, —SO-alkyl, —SO-substituted alkyl, —SO-aryl, —SO-heteroaryl, —SO$_2$-alkyl, —SO$_2$substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, cycloalkyl, cycloalkenyl, substituted alkyl, substituted alkoxy, substituted alkenyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heterocycle" or "heterocyclic" refers to a monoradical saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxylamine, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Illustrative examples of nitrogen heterocycles and heteroaryls are pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

The term "saccharide" refers to oxidized, reduced or substituted saccharides hexoses such as D-glucose, D-mannose, D-xylose, D-galactose, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as sucrose, lactose, or maltose; derivatives such as acetals, amines, acylated, sulfated and phosphorylated sugars; oligosaccharides having from 2 to 10 saccharide units. For the purposes of this definition, these saccharides are referenced using conventional three letter nomenclature and the saccharides can be either in their open or preferably in their pyranose form.

As to any of the above groups that contain one or more substituents, it is understod of course, that such groups do not contain any substitution or substitution patterns which are sterically impractical and/or synthetically non-feasible. In addition, the compounds of this invention include all stereochemical isomers and mixtures thereof arising from the substitution of these compounds.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The term "effective amount", means a dosage sufficient to provide treatment for the disease state being treated. This will vary depending on the patient, the disease and the treatment being effected.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartarate, mesylate, acetate, maleate, oxalate and the like.

The term "thiol-depleting compound" refers to a compound which upon administration to a host or to a cell, results in a global lowering of the concentration of available reduced thiol (e.g., glutathione). Examples of thiol-depleting compounds include buthionine sulfoximine ("BSO", a known inhibitor of glutathione synthesis), diethyl maleate (a thiol reactive compound) dimethyl fumarate, N-ethyl maleimide, diamide (diazene dicarboxylic acid bis-(N,N'-dimethylamide)) and the like.

The term "ionizing radiation" refers to radiation conventionally employed in the treatment of tumors which radiation, either as a large single dosage or as repeated smaller dosages, will initiate ionization of water thereby forming reactive oxygen species. Ionizing radiation includes, by way of example, x-rays, electron beams, γ-rays, and the like.

The term "oxalate" salts represents a dianion of oxalic acid, including its salts. Illustrative examples of oxalic acid salts include their sodium, potassium and ammonium salts. The term "oxalate precursors" represents compounds which undergo a chemical transformation (in the presence of a texaphyrin) to form the oxalic acid dianion, i.e., $O_2CCO_2^{2-}$. Illustrative examples of oxalate precursors are oxalic acid esters, oxalic acid diesters, ascorbate, dehydroascorbate, glyoxal, oxamates, oxamide(s), glycolates, and oxalyl chloride. It is understood that the preceding oxalate precursors, especially acids, can exist as their corresponding salts such as sodium, potassium and ammonium salts.

The term "porphyrin derivative" refers to those molecules which contain as part of their chemical structure a polypyrrole macrocycle.

The term "DNA alkylators" refer to well known alkylating agents which alkylate DNA thereby interfering with cellular processes and leading to cell death. Suitable alkylating agents include nitrogen mustards (e.g., mechlorethamine, cyclophosphamide, ifosfamide, mephalan, chlorambucil and estramustine), etheleneimines and methylmelamines (e.g., hexamethylmelamine and thiotepa), alkyl sulfonates (e.g., busulfan), nitroureas (e.g., carmustine, lomusine, semustine, and streptozocin), and triazines (e.g., dacarbazine, procarbazine, and aziridine).

Experimental

Methods

The following examples describe the reaction of GdTex with dehydroascorbic acid in buffered solution to provide the oxalate coordination complex of the invention, and the reaction of GdTex with (di)sodium oxalate to provide the same product. The cellular uptake of GdTex in the presence of ascorbate is also described.

General Procedure: General Protocol to Test for Formation of M-Tex Oxalate Complex in Buffer To a solution of motexafin gadolinium (131 μM) in 400 μL buffer (100 mM sodium chloride, 50 mM HEPES, pH 7.5) was added a 10-fold molar excess of neat (either solid or liquid) compound being tested as a source of oxalate. The UV-visible absorbance of the resulting solution was then monitored for 24 hours. The following species all resulted in formation of the characteristic absorbances at 510 nm and 780 nm: ascorbic acid, dehydroascorbic acid, oxalic acid, sodium oxalate, dimethyl oxalate, diethyl oxalate, dibutyl oxalate, di-tert-butyl oxalate, glyoxylic acid, glyoxal, oxamic acid, and oxamide (All compounds were purchased from Aldrich Chemical Co., Milwaukee, Wis., except for dehydroascorbic acid, which was obtained in dimeric form from Fluka Chemical Co., Milwaukee, Wis.).

General Description of Formation of M-Tex Oxalate Complexes in Buffer.

A 10 mM stock solution of sodium oxalate (Aldrich Chemical Co., Milwaukee, Wis.) in water was prepared by dissolving 13.4 mg in 10 mL of ACS grade water. Test solutions of various Texaphyrin metal cation complexes at 50 μM concentration in buffer (5 mM HEPES, pH 7.5, 10 mM sodium chloride) and sodium oxalate (1 mM, all concentrations final) were prepared by combining stock sodium oxalate, buffer, and Texaphyrin complex solutions and adding ACS grade water to 1 mL final volume. Test solutions were stored in the dark for 24 hours, whereupon the UV-vis spectra were measured. Spectra of the following texaphyrins were observed to have altered to form new absorbances characteristic of oxalate complex formation: motexafin europium(III), motexafin gadolinium(III), motexafin terbium(III), motexafin dysprosium(III), motexafin holmium(III), motexafin erbium(III), and motexafin lutetium(III). Spectra for all Texaphyrin oxalate complexes displayed absorbance maxima at 510 nm and 780 nm, regardless of the initial absorbance wavelengths of the Texaphyrin complex starting materials, which ranged from 474–478 nm and 732–746 nm.

EXAMPLE 1

Reaction of Motexafin Gadolinium (Gd-Tex) with Ascorbic Acid in Buffered Solution A solution of ascorbic acid (1.23 mM) in 50 mM HEPES buffer, pH 7.5, 100 mM NaCl (all concentrations final) was placed in a 1 mm quartz cuvette at ambient temperature. The UV-visible spectrum of this solution was recorded every 30 seconds following addition of a solution of Gd-Tex in ACS (American Chemical Society grade) water (62 μM final, 0.05 eq.). Buffer was treated with Chelex 100™ (BioRad Labs, Hercules, Calif.) prior to use, to remove endogenous transition metal cation contaminants. Within an hour after addition of Gd-Tex, the absorbance of ascorbate at 266 nm was observed to decrease. Moreover, the absorbance maxima of Gd-Tex at 470 nm and 740 nm were converted to new absorbance maxima at 510 nm and 780 nm, corresponding to formation of the oxalate coordination polymer of Gd-Tex.

EXAMPLE 2

Reaction of Motexafin Gadolinium (Gd-Tex) with Dehydroascorbic Acid in Buffered Solution Motexafin gadolinium (Gd-Tex, 50 mg, 43.6 µmol) was placed in a 50 mL round bottom flask and dissolved at room temperature in ACS grade water (20 mL). Dehydroascorbic acid (DHA, 15.3 mg, 87.9 µmol) (Aldrich Chemical, Milwaukee, Wis.) was placed in a 15 mL screw-cup vial and buffer (10 mL, 100 mM NaCl, 50 mM HEPES, pH=7.5) was added. Sonication for 10 min at 25° C. produced very fine yellow suspension. This suspension was added at once to the above aqueous solution of Gd-Tex and agitated as it was heated to about 50° C. using a water bath under ambient atmosphere. Progress of the reaction was followed by monitoring the increased absorbance in the UV-visible spectrum at 780 nm. After about 75 minutes, and after no further changes in the spectrum were observed, another portion of solid DHA (15.3 mg, 87.9 µmol) was added to the reaction mixture, and the resulting reaction mixture was agitated for about 18 h. The reaction was judged to be complete as evidenced by the complete conversion of the Q-like absorbance band from 740 nm to 780 nm. Within several hours upon cooling to ambient temperature, a very fine dark-brown precipitate was observed in the reaction flask. This precipitate was isolated by centrifugation at 10° C. and 15,000 r.p.m. for 25 min and removal of supernatent. The pellet was resuspended and centrifuged with ACS grade (×5) to remove salts and other impurities, and then dried under vacuum at 50° C. for 4 days.

Elemental Analysis: Anal. Calcd. for $[C_{48}H_{66}N_5O_{10}Gd](C_2O_4)(H_2O)$: C, 52.85; H, 6.03; N, 6.16; Gd, 13.84. Found: C, 52.47; H, 6.01; N, 5.65; Gd, 12.33.

Elemental analysis is based on a 1:1 ratio of the components representing structural units "A" and "B" in the coordination polymer.

EXAMPLE 3

Reaction of Motexafin Gadolinium with Sodium Oxalate in Aqueous Solution

Motexafin gadolinium (200 mg, 174 µmol) was placed into a 250 mL Erlenmeyer flask and dissolved in ACS grade water (50 mL). Sodium oxalate (233 mg, 1.74 mmol) was dissolved in ACS grade water (10 mL) in a vial, and then added drop wise over 5 minutes to the above solution of Gd-Tex. The reaction mixture, which immediately changed color from deep-green to brown, was allowed to stir for about an hour. The resulting suspension was divided into 4 polypropylene tubes and centrifuged at 15,000 r.p.m. for 2 hours. The pellet was resuspended and centrifuged with ACS grade water five times to remove salts and other impurities, and then dried under vacuum at 50° C. for 4 days to provide the oxalate complex of Gd-Tex as a brown-green powder (70 mg). The UV-visible absorbance spectrum indicated complete conversion of the Q-like absorbance band from 740 nm to 780 nm.

Elemental Analysis: Anal. Calcd. for $[C_{48}H_{66}N_5O_{10}Gd](C_2O_4)(H_2O)_2$: C, 52.85; H, 6.03; N, 6.16; Gd, 13.84. Found: C, 51.00; H, 6.04; N, 6.13; Gd, 13.04.

Elemental analysis is based on a 1:1 ratio of the components representing structural units "A" and "B" in the coordination polymer.

This procedure was repeated using oxalic-$^{13}C_2$ acid dihydrate (Aldrich) in buffer. The $^{13}C$ NMR spectrum on the resulting material contained a resonance at δ 213.6 (singlet). This singlet indicates that carbon from the labeled oxalate is incorporated into the Gd-Tex oxalate complex (coordination polymer), and is in a symmetrical environment.

The following structures represent a turmeric form of the coordination polymer of the present invention:

Structure 1 (GdTex plus oxalate)

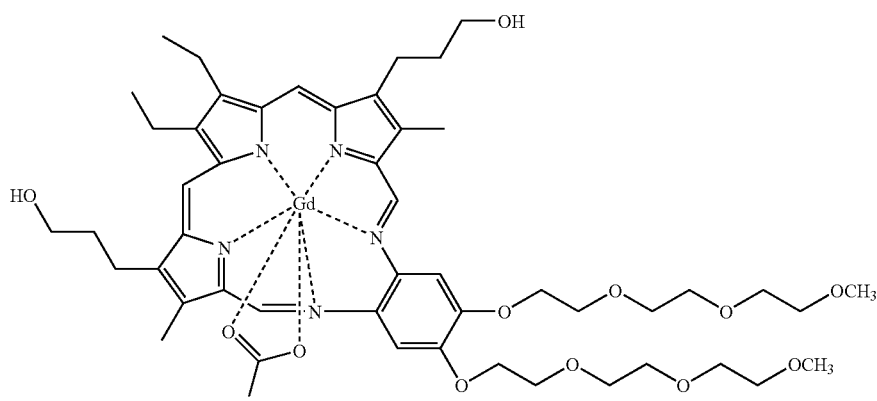

-continued
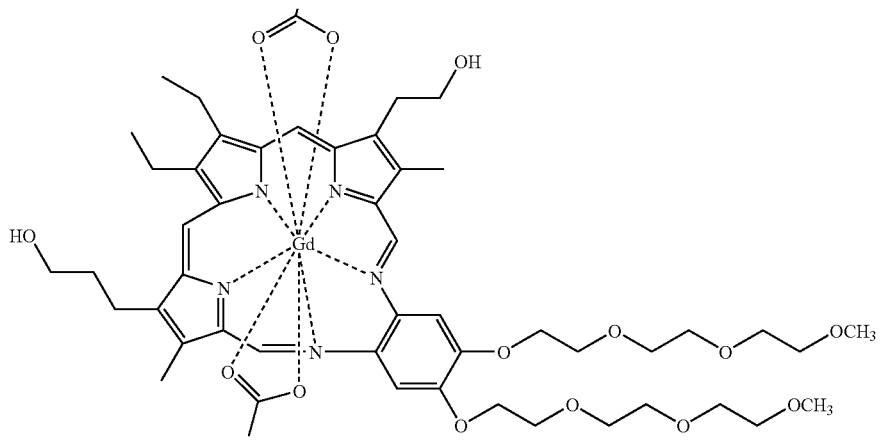
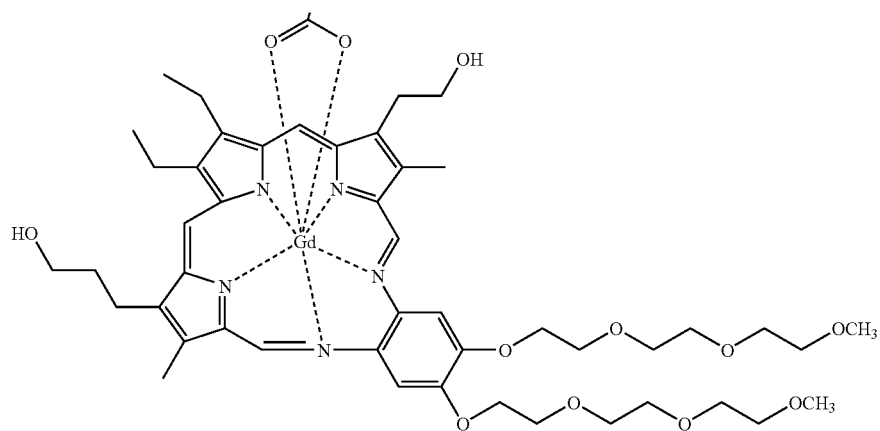
M represents Gd
Structure 2 (GdTex plus oxalate)
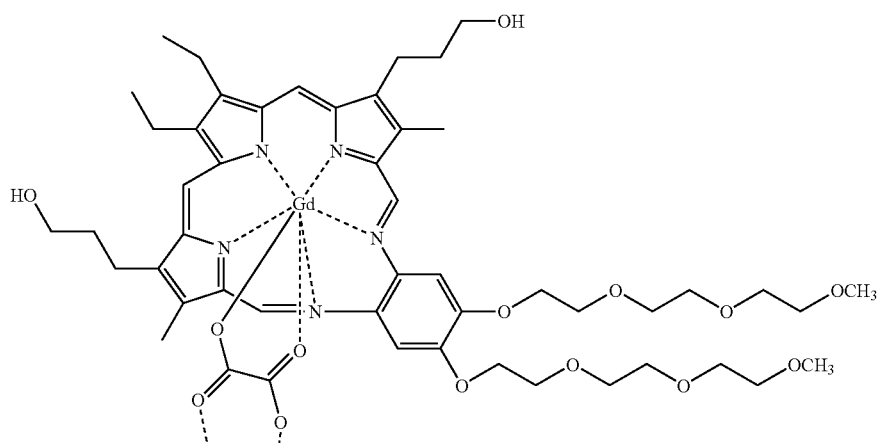

-continued
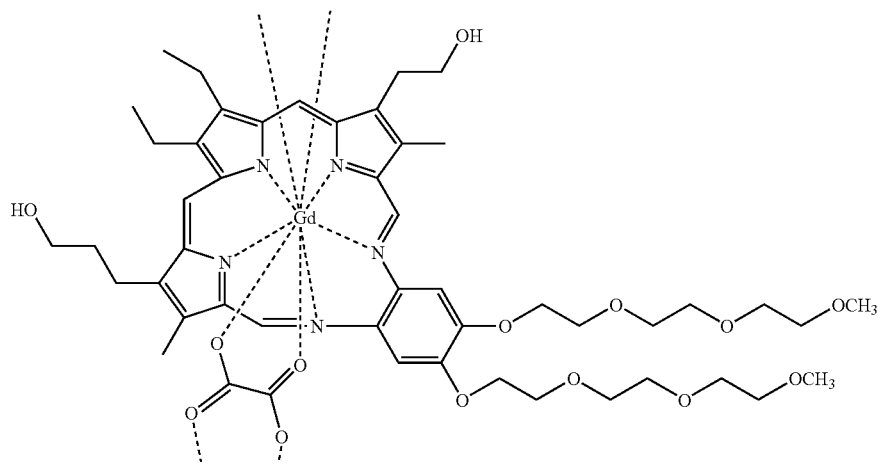
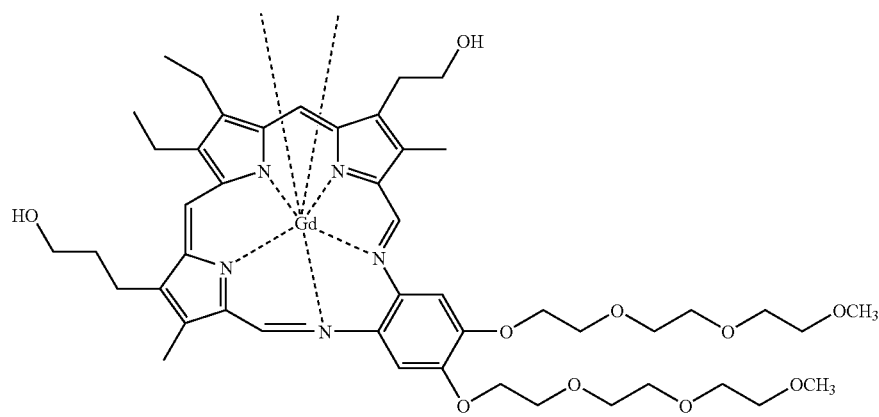
M represents Gd
Structure 3 (LuTex oxalate)
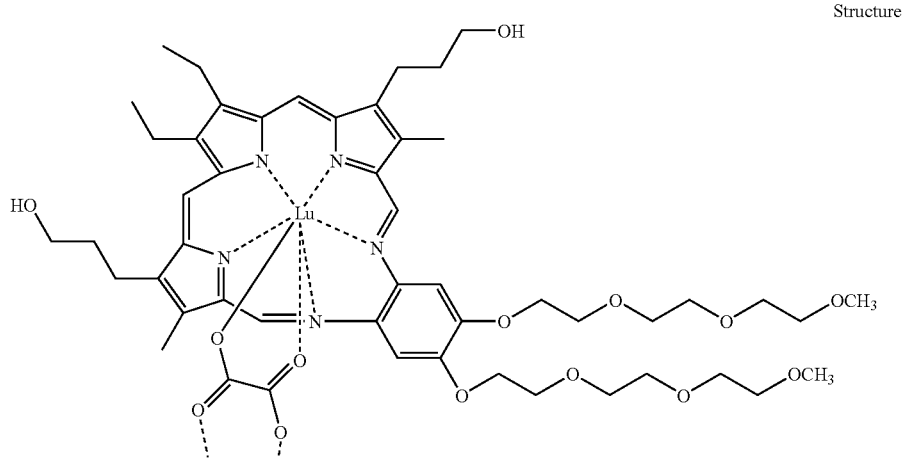

-continued
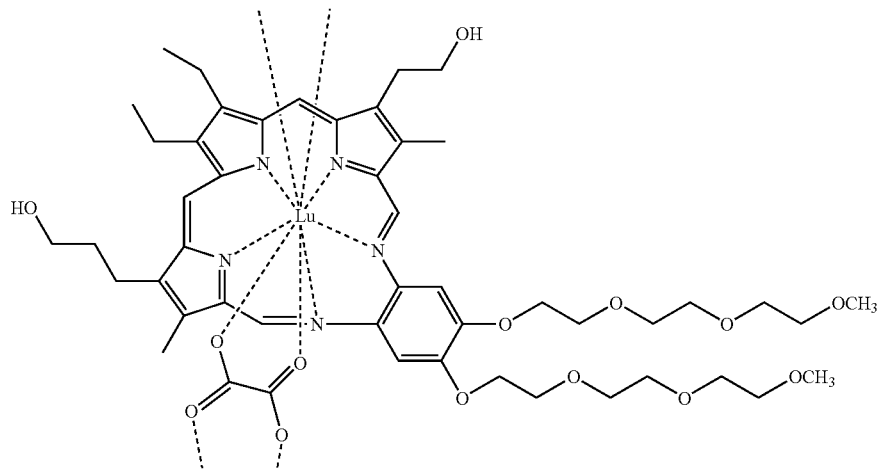
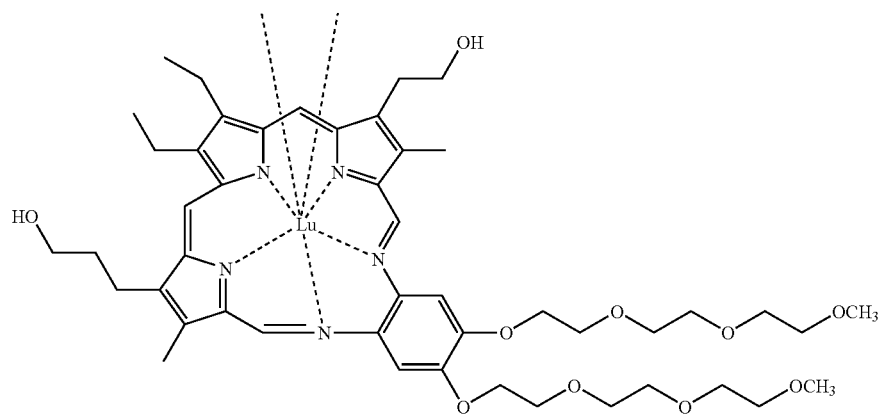
M represents Lu
Structure 4 (LuTex plus oxalate)
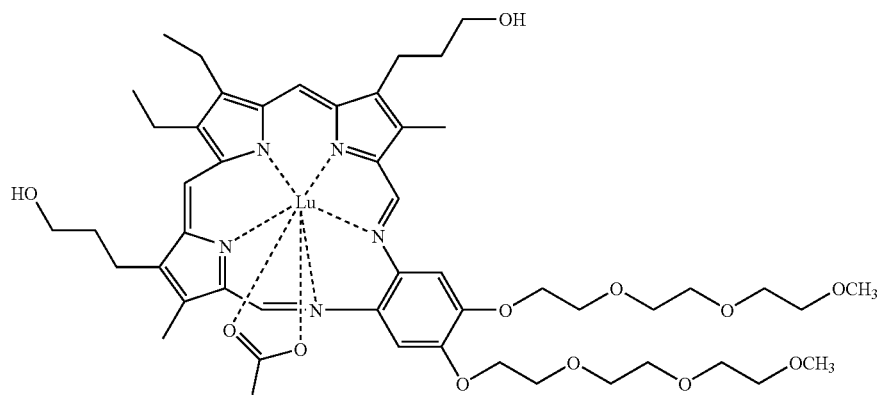

-continued
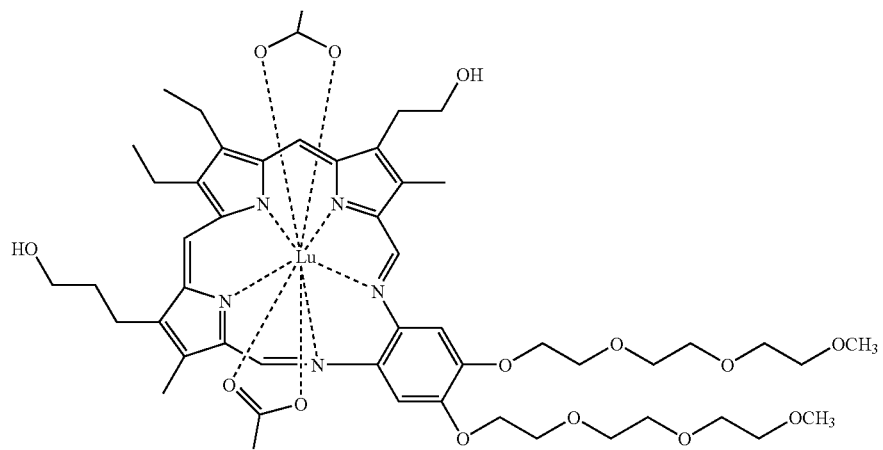
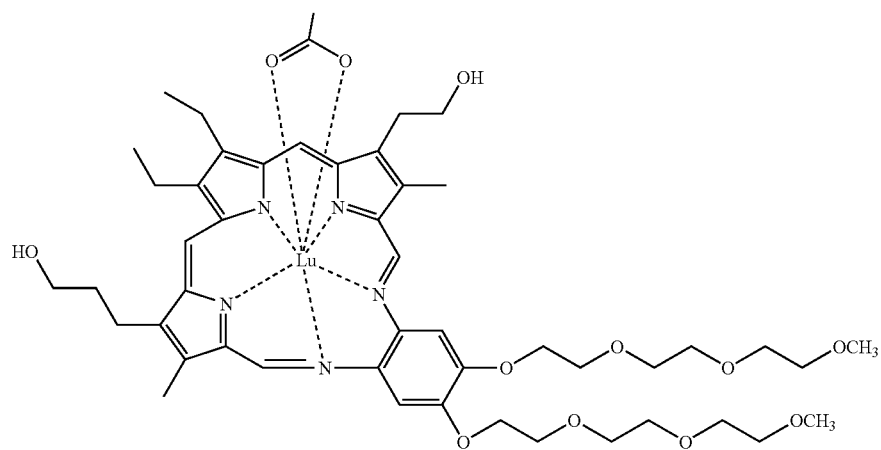
M represents Lu
Structure 5
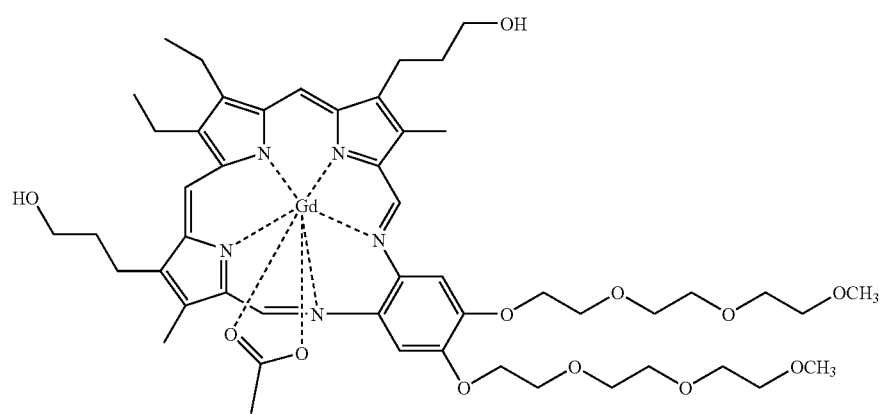

-continued
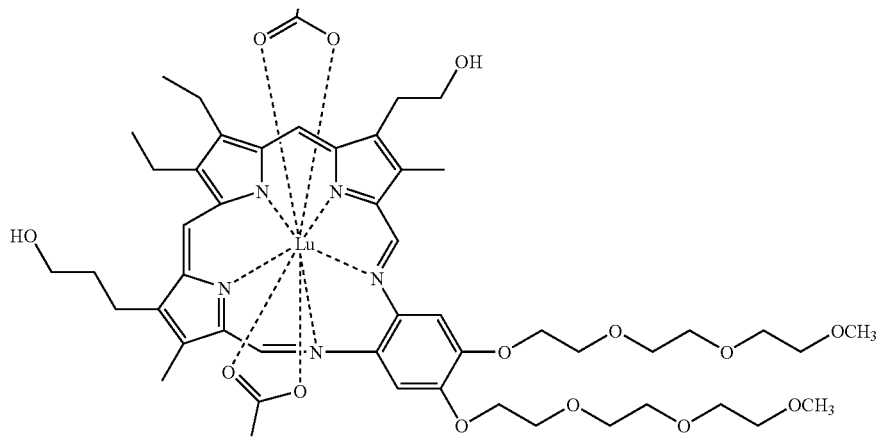
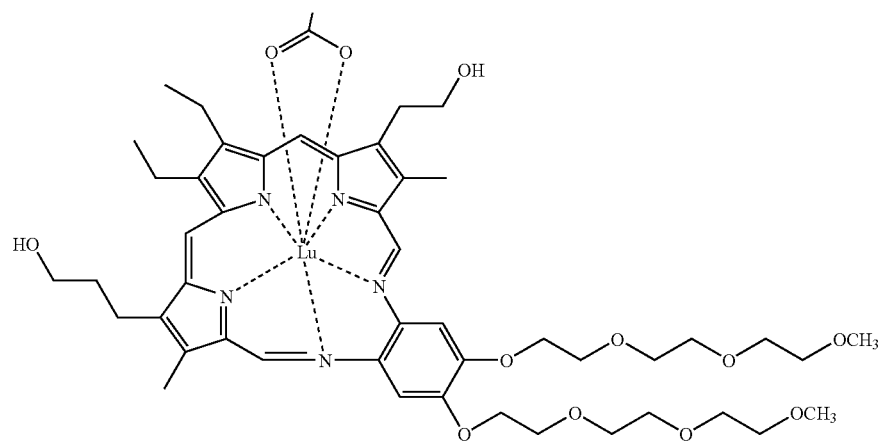
M independently at each occurrence represents Gd or Lu
Structure 6
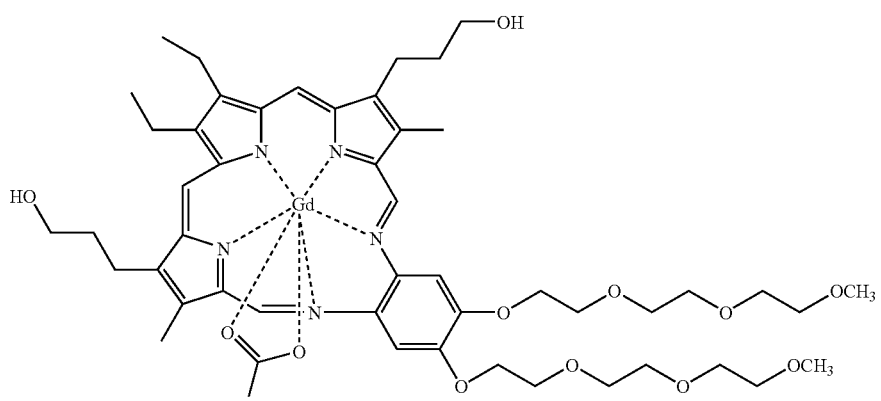

-continued
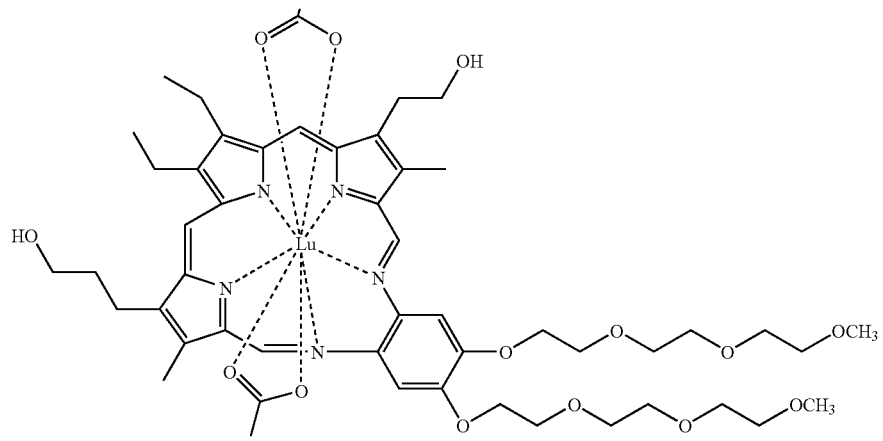
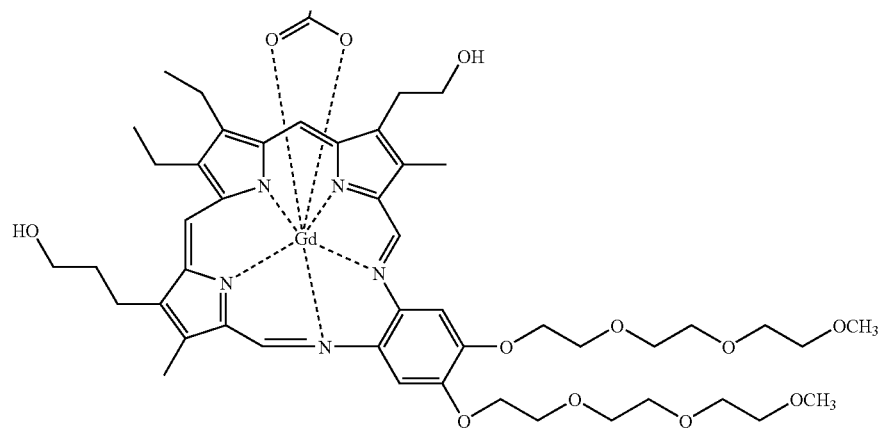
M independently at each occurrence represents Gd or Lu
Structure 7
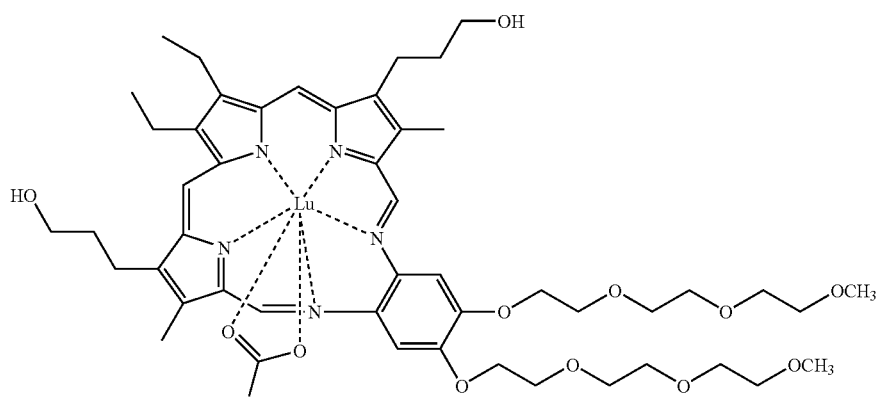

-continued
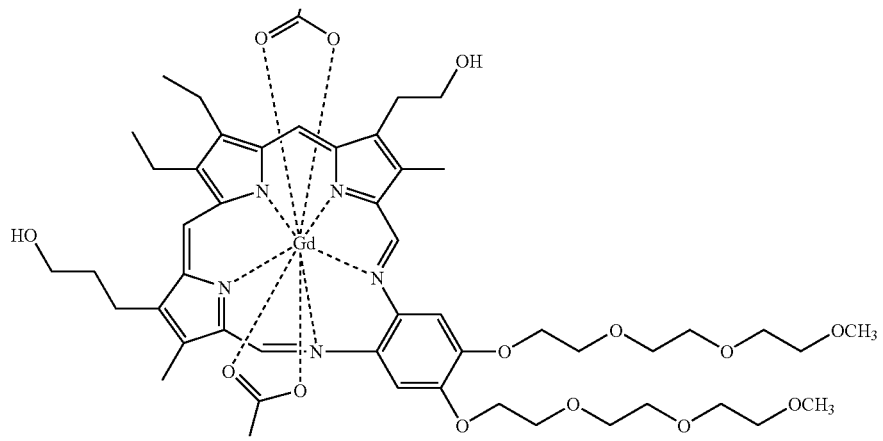
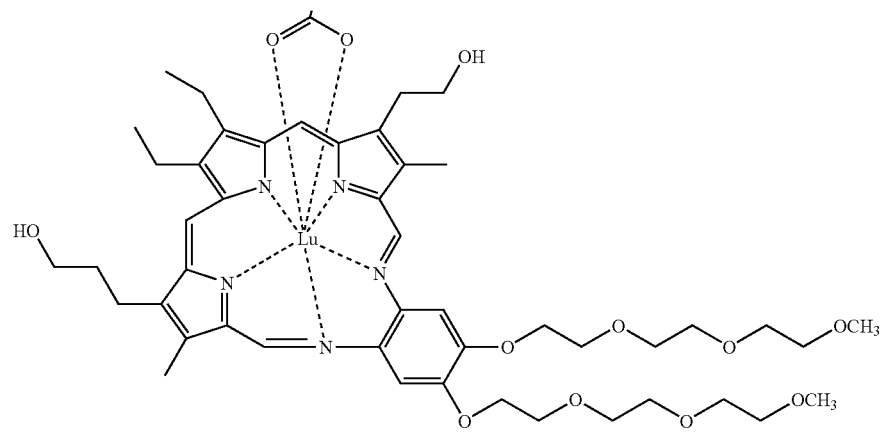
M independently at each occurrence represents Gd or Lu
Structure 8
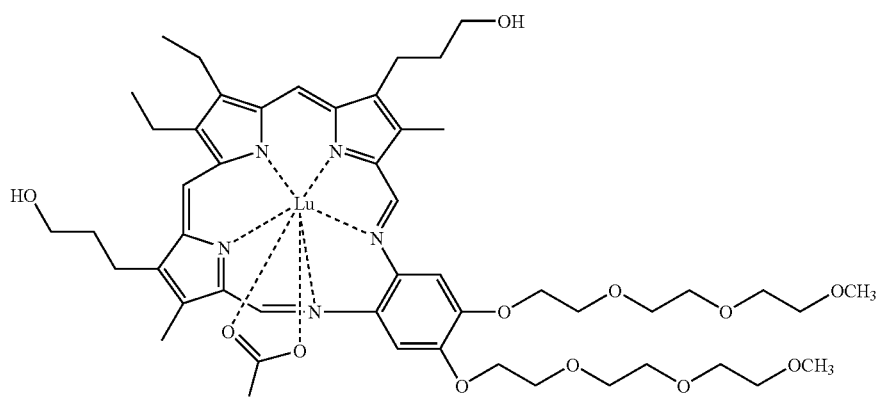

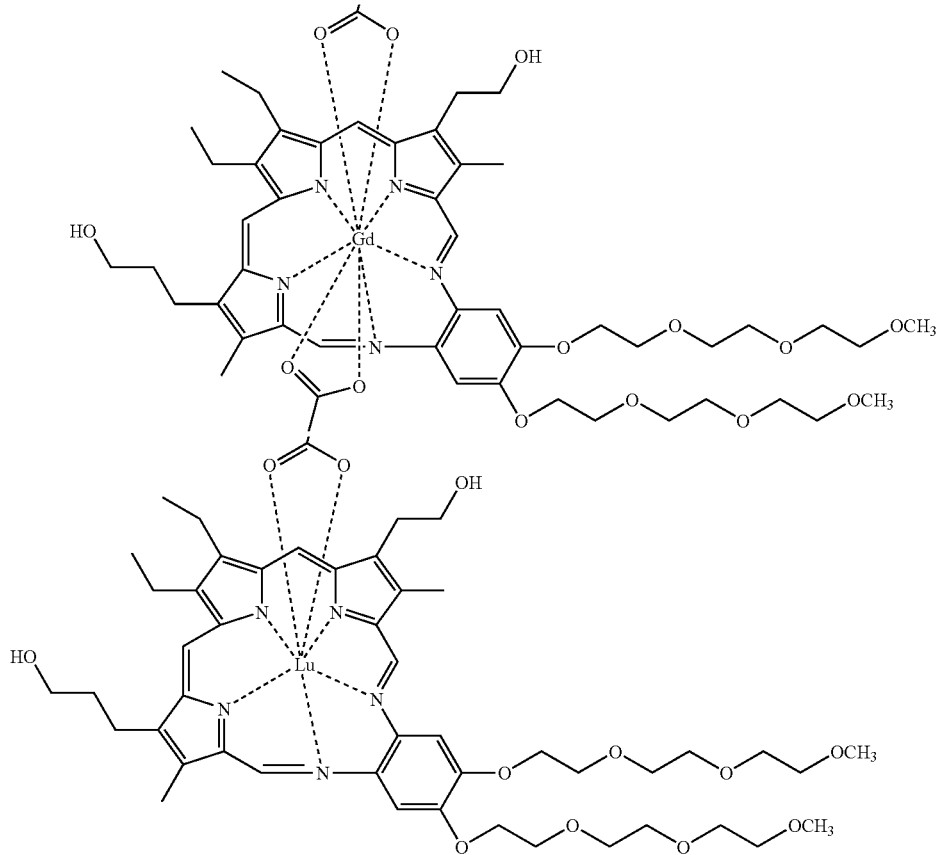

M independently at each occurrence represents Gd or Lu

EXAMPLE 4

Formation of a Copolymer Comprised of Gd-Tex and Lu-Tex and Oxalate in Buffer

A 10 mM stock solution of sodium oxalate (Aldrich Chemical Co., Milwaukee, Wis.) in water was prepared by dissolving 13.4 mg in 10 mL of ACS grade water. A mixture of Gd-Tex and Lu-Tex at 50 μM concentration each in buffer (50 mM HEPES, pH 7.5, 100 mM sodium chloride, all concentrations final) was prepared by adding stock texaphyrin complex solutions to buffer and adding ACS grade water to 900 μL final volume. The resulting mixture was agitated by vortexing to form a homogeneous solution and allowed to stand at ambient temperature for 5 minutes, whereupon an aliquot of sodium oxalate stock solution (100 μL, 1 mM final concentration) was added to the texaphyrin solution, which was again agitated by vortexing. This solution was stored in the dark for 10 minutes, whereupon the UV-vis spectrum was measured. The spectrum was observed to have altered to form new absorbance maxima characteristic of oxalate complex formation at 510 nm and 780 nm, accompanied by the loss of the initial absorbance wavelength maxima of the Gd-Tex and Lu-Tex starting materials (at ca. 468 and 737 nm, measured prior to oxalate addition).

EXAMPLE 5

Stability of the 780 nm Species in Human Serum

The stability of the 780 nm species in human serum was tested by adding 0.11 mg of the 780 nm species to 0.7 mL of blank human serum in a polystyrene container. The sample was agitated vigorously to facilitate dissolution of solids. When it appeared that the majority of the material was in solution, a small volume was transferred to a 1 mm Quartz cuvette and UV-vis scans were performed periodically for 7 hours. The cuvette was maintained at 37° C. in a humidified incubator under a 5% $CO_2$ atmosphere between scans. UV-vis spectra were obtained. The majority of 780 nm species was still present after 7 hours, indicating that the coordination polymer was intact.

EXAMPLE 6

Determination of Absorption of GdTex and LuTex

The absorption of GdTex and LuTex, using different sources of the respective texaphyrin, in HepG2 cells was determined, by comparing absorption for GdTex and LuTex in the cell line in medium alone, in medium containing ascorbic acid, and using GdTex and LuTex that had been premixed with ascorbate for a period of time before exposure to the cell line.

Materials
Pipettes
DI water
pH paper (EM Reagents)
L-Ascorbic Acid (Sigma)
Motexafin Gadolinium Injection (2 mM in 5% mannitol)
Motexafin Lutetium Injection (2 mg/mL in 5% mannitol)
Catalase Roche Molecular Biochemicals, Indianapolis, Ind., 260,000 unit/ml))
2.5 mM ascorbic acid in water
5% Mannitol
Balance: Mettler AT201
1.5 ml polypropyline centrifuge tubes (VWR Scientific, San Francisco, Calif.)
NUNC 4.5 ml cryotubes (VWR)
15 mL polypropylene centrifuge tubes (VWR)

Cell Line

The HepG2 tumor cell line, a hepatocellular carcinoma, was obtained from the American Type Culture Collection (ATCC), Manassas, Va. (Catalog # HB-8065). The HepG2 cells were maintained in Eagle's Minimal Essential medium with Earl's BSS and 2 mM L-glutamine (EMEM) that is modified by ATCC to contain 1.0 mM sodium pyruvate, 0.1 mM nonessential amino acids, and 1.5 g/L sodium bicarbonate (ATCC, Cat. # 30-2003) and supplemented with 10% fetal bovine serum (FBS) FBS (Hyclone, Logan, Utah, Lot # AHF8559) and 100 U penicillin/100 ug/ml streptomycin (Sigma, St. Louis, Mo.). Cells are fed one to two times weekly and passed at 3,000,000 cells per 75 cm tissue culture flask (Costar). Cells are passed using 0.25% trypsin, 0.02% EDTA solution (50/50 PBS/trypsin (Sigma)). Cells used were at the 96th passage at the time of use.

Methods

GdTex Cell Association Study

HepG2 Cells were plated at a density of 500,000 cells per dish in 100 mm tissue culture dishes containing 10 mL of RPMI media (Gibco, Rockville, Md.) supplemented with 10% Fetal Bovine Serum (Lot # AJC9908, and 100 U/mL penicillin/100 ug/mL streptomycin (Lot # 50K2308, Sigma, St. Louis, Mo.). Cells were plated out 1–2 days prior to treating with motexafin gadolinium.

The day prior to treating the dishes with GdTex (9-19-00), an "aged" solution was prepared containing 50 μM GdTex, 100 μM ascorbate, and Catalase (at a concentration 1:1000 of the stock solution concentration provided by the vendor). This solution was incubated at 37° C. 5% $CO_2$ for approximately 24 hr prior to addition to the appropriate test dishes.

On the day of treatment, test solutions were prepared as shown in the Table I below in pre-incubated medium. The pre-incubated medium was equilibrated at 37° C. in 5% $CO_2$ for at least 1 hour prior to use for making each test solution. To the pre-equilibrated medium, the catalase was added first (if indicated) and mixed, then the ascorbate (if indicated) was added and mixed. The GdTex (if indicated) was added last followed by a final mix. Within one hour of preparation, the medium was removed from each dish are replaced with 10 mL of appropriate test solution. Each condition was tested in three replicate dishes, except for the no-cells controls, for which 2 dishes were used. No-cell controls were prepared by adding 10 mL of the appropriate solution to an empty dish that did not contain any cells.

TABLE I

| Test Article | Vol. 5% Mannitol (mL) | Vol. 2 mM GdTex- (mL) | Vol. Asc. (mL) | Vol. 10X Cat. (mL) | Vol. RPMI (mL) | Total Vol. (mL) | GdTex Conc. (μM) | Asc. Conc. (μM) | Cat. Conc. (X) |
|---|---|---|---|---|---|---|---|---|---|
| Control | 3 | N/A | 4.8 | 12 | 100.20 | 120 | 0 | 100 | 1 |
| Gd-Tex | | 3 | N/A | N/A | 117.0 | 120 | 50 | 0 | 0 |
| Gd-Tex + Asc | | 3 | 4.8 | N/A | 112.2 | 120 | 50 | 100 | 0 |
| Gd-Tex + Asc + Catalase | | 3 | 4.8 | 12 | 100.2 | 120 | 50 | 100 | 1 |
| Gd-Tex + Asc + Catalase (aged) | | 3 | 4.8 | 12 | 100.2 | 120 | 50 | 100 | 1 |

LuTex Cell Association Study

HepG2 Cells were plated at a density of 500,000 cells per dish in 100 mm tissue culture dishes containing 10 mL of RPMI media (Gibco, Rockville, Md.) supplemented with 10% Fetal Bovine Serum (Lot # AJC9908, and 100 U/mL penicillin/100 ug/mL streptomycin (Lot # 50K2308, Sigma, St. Louis, Mo.). Cells were plated out 1–2 days prior to treatment with motexafin gadolinium.

The day prior to treating the dishes with LuTex, two "aged" solutions were prepared as shown in Table II below. These two solutions were incubated at 37° C. in 5% $CO_2$ for approximately 23 hr prior to addition to the appropriate test dishes.

TABLE II

| Test Article | Vol. 5% Mannitol (mL) | Vol. 2 mg/mL LuTex (mL) | Vol. 2.5 mM Asc. (mL) | Vol. 10X Cat. (mL) | Vol. RPMI (mL) | Total Vol. (mL) | LuTex Conc. (μM) | Asc. Conc (μM) | Cat. Conc (X) |
|---|---|---|---|---|---|---|---|---|---|
| Lu-Tex + Catalase (aged) | N/A | 3.5 | N/A | 12 | 104.5 | 120 | 50 | 0 | 1 |

TABLE II-continued

| Test Article | Vol. 5% Mannitol (mL) | Vol. 2 mg/mL LuTex (mL) | Vol. 2.5 mM Asc. (mL) | Vol. 10X Cat. (mL) | Vol. RPMI (mL) | Total Vol. (mL) | LuTex Conc. (µM) | Asc. Conc (µM) | Cat. Conc (X) |
|---|---|---|---|---|---|---|---|---|---|
| Lu-Tex + Asc + Catalase (aged) | N/A | 3.5 | 4.8 | 12 | 99.7 | 120 | 50 | 100 | 1 |

On the day of treatment, test solutions were prepared as shown in Table III below in pre-incubated media. The pre-incubated median was equilibrated at 37° C. in 5% $CO_2$ for at least 1 hour prior to use for making each test solution. To the pre-equilibrated media, the catalase was added first (if indicated) and mixed, then the ascorbate (if indicated) was added and mixed. The LuTex (if indicated) was added last followed by a final mix. Within 30 min of preparation, the media was removed from each dish replaced with 10 mL of appropriate test solution. Each condition was tested in three replicate dishes, except for the no-cells controls, for which 2 dishes were used. No-cell controls were prepared by adding 10 mL of the appropriate spiking solution to an empty dish that did not contain any cells.

The pellet was then transferred to a fresh 15 mL polypropylene centrifuge tube (TUBE 2). A second 1 mL of PBS was added to TUBE 1, pipetted up and down, and then transferred to TUBE 2 using a fresh tip. Eight mL of PBS was then added to TUBE 2 to bring the final volume to 10 mL. TUBE 2 was centrifuged at 23° C. for 10 min at 3800 rpm using a Beckman GH-38 rotor. The pellet was suspended in 0.5 mL of PBS and the volume transferred to a 6 mL disposable polypropylene test tube (TUBE 3). A second 0.5 mL volume of PBS was added to TUBE 2, and then transferred to TUBE 3 (using a fresh tip) to complete the transfer. The final cell suspension (TUBE 3) was placed in storage at −80° C. for storage until the time of analysis.

TABLE III

| Test Article | 5% Mannitol (mL) | Lu-Tex (mL) | Asc. (mL) | 10X Cat. (mL) | Vol. RPMI (mL) | Total Vol. (mL) | Lu-Tex Conc. | Asc. Conc. | Cat. Conc (X) |
|---|---|---|---|---|---|---|---|---|---|
| Ctrl | 3.5 | N/A | 4.8 | 12 | 99.7 | 120 | 0 | 100 | 1 |
| Lu-Tex | | 3.5 | N/A | N/A | 116.5 | 120 | 50 | 0 | 0 |
| Lu-Tex + Asc | | 3.5 | 4.8 | N/A | 111.7 | 120 | 50 | 100 | 0 |
| Lu-Tex + Asc + Cat | | 3.5 | 4.8 | 12 | 99.7 | 120 | 50 | 100 | 1 |
| Lu-Tex + Catalase (aged) | | 3.5 | 4.8 | 12 | 99.7 | 120 | 50 | 100 | 1 |
| Lu-Tex + ASC + Catalase (aged) | | 3.5 | 4.8 | 12 | 99.7 | 120 | 50 | 100 | 1 |

Cell Harvesting and Analysis

GdTex Cell Association Study

At the end of the four hour incubation period, four 1 mL samples of test solution were aliquoted into four microcentrifuge tubes for further analysis. The test solution was then completely aspirated from each dish, and then each dish was rinsed 3 times with 10 mL PBS. After aspirating the final 10 mL rinse, one mL PBS was added to each dish and a sterile cell scraper was used to release the cells from the dish. The amount of time between the start of washing and completion of the scraping process was approximately 1 hour. Because the cells tended to float, it was necessary to use multiple PBS washes (e.g. 5 to 10 small volumes) in order to transfer all of the cells into a 15 mL polypropylene centrifuge tube (Labeled as TUBE 1). TUBE 1 was brought to a final volume of 15 mL and then centrifuged at 23° C. for 10 min @ 3800 rpm using a Beckman GH-38 rotor. The supernatant was poured off and the cell pellet was resuspended in 1 ml of PBS (still in TUBE 1) by pipetting up and down. Additional PBS was added to bring the final volume to 10 mL. Centrifugation was repeated using the same conditions specified above, and the supernatant was decanted. The cell pellet was resuspended in 1 mL of PBS by pipeting up and down.

For the t=4 hours dishes, all steps were done as indicated above. However, for the t=0 dishes, all steps were done as described above, except the transfer to TUBE 2 and subsequent 10 mL wash was not done. The transfer to Tube 1 (in 15 mL PBS), centrifugation, decanting, and 10 mL wash were all done in TUBE 1 as described above. However, after decanting after the. 10 mL wash, the cell pellet was transferred directly from TUBE 1 to TUBE 3 for final analysis using two 0.5 mL rinses. When transferring cells, a fresh tip was used for adding the PBS, whereas the original pipette tip was used for actually transferring the cells to the next tube.

LuTex Cell Association Study

At the end of the four hour incubation period, four 1 mL samples of test solution were aliquoted into four microcentrifuge tubes for further analysis. The test solution was then completely aspirated from each dish, and then each dish was rinsed 3 times with 10 mL PBS. After aspirating the final 10 mL rinse, one mL PBS was added to each dish and a sterile cell scraper was used to release the cells from the dish. The amount of time between the start of washing and completion of the scraping process was approximately 1 hour. Because the cells tended to float, it was necessary to use multiple PBS washes (e.g. 5 to 10 small volumes) in order to transfer all of the cells into a 15 mL polypropylene centrifuge tube (Labeled as TUBE 1). TUBE 1 was brought to a final volume of 15 mL PBS and then centrifuged at 23° C. for 10 min at 3800 rpm using a Beckman GH-38 rotor. The supernatant was poured off and the cell pellet was resuspended in 1 mL of PBS (still in TUBE 1). The pipette tip used for resuspending the cells was rinsed two times by pipetting two 1 mL volumes of PBS into the open end of the tip and collecting the rinse into TUBE 1. Additional PBS was added to bring the final volume to 10 mL. Centrifugation was repeated using the same, conditions specified above, and the supernatant was decanted.

The cell pellet was then resuspended in 1 mL of PBS by pipetting up and down. The pellet was then transferred to a fresh 15 mL polypropylene centrifuge tube (TUBE 2). A second 1 mL of PBS was added to TUBE 1, pipetted up and down, and then transferred to TUBE 2 using the original tip. An additional 1 mL wash was done in an identical manner, and finally, a third 1 mL PBS volume was added to the open end of the original tip and collected into TUBE 2. PBS was then added to TUBE 2 to bring the final volume to 10 mL. TUBE 2 was centrifuged at 23° C. for 10 min at 3800 rpm using a Beckman GH-38 rotor. The pellet was suspended in 0.25 mL of PBS and the volume transferred to a 6 mL disposable polypropylene test tube (TUBE 3). Two more rinses of TUBE 2 were done, each using 0.25 mL of PBS with transfers done using the original tip. Therefore, the final volume in TUBE 3 was approximately 0.75 mL. The final cell suspension (TUBE 3) was placed in storage at −80° C. for storage until the time of analysis. When transferring cells, a fresh tip was used for adding the PBS, whereas the original pipette tip was used for actually transferring the cells to the next tube.

Results

Four hours after incubation, a sample of the supernatant was removed from selected dishes and a UV-vis spectrum taken. The percentage of drug that had precipitated for each condition was estimated by comparing the absorbance at 740 nm in the each group with that obtained for the group spiked with GdTex alone. A visible pellet was only observed for the GdTex+ascorbate+catalase (aged) group. Based on the decrease in absorbance at 740 nm, the percentage precipitated for this group was estimated to be 60–63% over the 4 hour period of the study.

A similar analysis was performed for the spiking solutions used in the LuTex study. A visible pellet was only observed for the LuTex+catalase (aged) and the LuTex+ascorbate+catalase (aged) groups. Based on the decrease in absorbance at 730 nm, the percentage precipitated for the LuTex+ascorbate+catalase (aged) group was estimated to be 24–31% over the 4 hr period of the study.

UV-Vis spectra were obtained in order to determine if a 780 nm absorbing species was present in the spiking solutions as part of the GdTex cell association study. 780 nm absorbing species was present both at the time of spiking and after four hours in the GdTex+ascorbate+catalase (aged) group. However, this species was reduced after centrifugation at 16,000×g for 30 minutes, suggesting that a significant percentage of the 780 nm absorbing material was present as a precipitate. Similar results were obtained for the LuTex cell association study. Interestingly, the 780 nm species was not observed for the LuTex+catalase (aged) group even though a small pellet was visible after centrifugation. This result suggests that the precipitate formed in this solution may have a different composition than that seen in the LuTex+ascorbate+catalase (aged) group. Alternatively, the amount of precipitate may have been too small to generate significant absorbance at 780 nm. However, it was noted that the final cell pellets obtained in PBS for these two groups were different shades of color (reddish brown and greenish black, respectively), suggesting that the composition of the precipitate may have been different between the two groups.

UV-vis spectra obtained of the cell pellets in the GdTex study, resuspended in PBS, showed that significant absorbance in the 700–850 nm region of the spectrum was seen only for the GdTex+ascorbate+catalase (aged) group. This was consistent with the fact that there was relatively little cell association in the other groups. Furthermore, the spectra suggested that the majority of the material associated with the cells was the 780 nm absorbing material. Similar results were obtained in the LuTex study, except both 730 and 780 nm absorbing species were observed in the LuTex+ascorbate+catalase (aged) group.

Shown by these experiments is that GdTex association with HepG2 cells was smaller that corresponding LuTex cell association with this cell line in the absence of ascorbate. However, for freshly prepared solutions made in the presence of ascorbate, GdTex and LuTex showed comparable levels of association. For the aged solutions, the GdTex+ascorbate+catalase (aged) group showed much greater uptake compared to the LuTex+ascorbate+catalase (aged) group.

EXAMPLE 7

Cellular Uptake of Gd-Tex Oxalate Complex In Vitro

Human uterine cancer cell line MES-SA cells (Harker W G, MacKintosh F R, Sikic B I *Cancer Res* 1983;43:4943–4950) were allowed to adhere to a 96-well microtiter plate (20,000 cells per well) overnight in 180 μL McCoys 5A medium supplemented with 10% fetal bovine serum. Stock sodium oxalate (Aldrich Chemical, St. Louis, Mo., 1.0 mM in medium, 90 μL) was serially diluted (1:3) in rows B through F (discarding the final 90 μL). Row G was used for no-oxalate control. Stock solutions of Gd-Tex (2 mM in water) diluted in medium were prepared and added to the plates to give a final volume of 200 μL in all wells. Columns 2 and 3 contained 100 μM Gd-Tex; columns 4–7 contained 75 μM Gd-Tex, columns 8 and 9 contained 25 μM Gd-Tex; and columns 10 and 11 contained no Gd-Tex (all concentrations final). The plates were incubated at 37° C. under a 5% $CO_2$/95% air atmosphere. Complex-containing medium was exchanged for fresh medium after 49 hours, whereupon medium was removed and cells were washed with phosphate buffered saline (180 μL). Phosphate buffered saline (supplemented with 10 mM KCl, 1 mM $MgCl_2$, 1 mM $CaCl_2$ and 20 mM glucose, 100 μL) was added to the plate and the absorbance was measured using a plate reader (VMax, Molecular Devices) at 510 nm–650 nm.

In a separate experiment, MES-SA cells (20,000 cells/well) were plated in a 96-well plate and allowed to adhere overnight in 180 μL McCoys 5A medium supplemented with 10% fetal bovine serum. Stock sodium oxalate (1.0 mM in medium (90 μL) was serially diluted (1:3) in rows B through F (discarding the final 90 μL). Row G was used for no-oxalate control. Stock solutions of Gd-Tex (2 mM in water) diluted in medium were prepared and added to the plates to give a final volume of 200 μL in all wells. Columns 2 and 3 contained 50 μM Gd-Tex; columns 4–5 contained 37.5 μM Gd-Tex, columns 6–7 contained 25 μM Gd-Tex, columns 8 and 9 contained 12.5 μM Gd-Tex; and columns 10 and 11 contained no Gd-Tex (all concentrations final). The plates were incubated at 37° C. under a 5% $CO_2$/95% air atmosphere. Complex-containing medium was exchanged for fresh medium after 24 hours, whereupon medium was removed and cells were washed with phosphate buffered saline (180 μL). Dichlorofluorescin acetate (DCFA, 5 μg/mL, Sigma Chemical, St. Louis, Mo.) in phosphate buffered saline (supplemented with 10 mM KCl, 1 mM $MgCl_2$, 1 mM $CaCl_2$ and 20 mM glucose, 100 μL) was added to the plate and the plate was returned to the incubator for 13 hours. The fluorescence was measured using a fluorescent plate reader (Fluoroskan, LabSystems, Inc.) using 485 nm excitation and 538 nm emission wavelengths (Rosenkranz A R, Schmaldienst S, Stuhlmeier K M, et al. *J Immunol Meth* 1992;156:39–45).

Incubating cells in the presence of both Gd-Tex and oxalate resulted in cell uptake of Gd-Tex oxalate complex, as evidenced by the increased absorbance due to the drug at 510–650 nm. Under similar conditions, a dichloroflorescein fluorescence was observed which was proportional to concentrations of oxalate and Gd-Tex in the medium. These results demonstrate that cellular uptake of Gd-Tex oxalate complex is more facile than the uptake of Gd-Tex, and that the compound thus taken up by cells may indirectly be measured by a corresponding increase in dichlorofluorescin oxidation, or directly by its absorbance at 510–650 nm.

EXAMPLE 8

The Cellular Uptake of the Gadolinium(III) Complex of Texaphyrin in the Presence of Ascorbate and Gd-Tex Oxalate Complex (Coordination Polymer)

Human lung cancer cells A549 were plated in 5 cm petri dishes in RPMI 1640 medium containing 15% fetal bovine serum and allowed to grow until 60% confluent. Cultures were then treated for 19 hours with: 1. Nothing (Control group). 2. 50 M Gd-Tex. 3. 50 M Gd-Tex and 60 M ascorbate. 4. 50 M Gd-Tex for 16 hours, followed by 50 M Gd-Tex oxalate complex for 3 hours. Cultures were washed twice with Dulbecco's phosphate buffered saline and then incubated in Hank's buffered saline solution containing either no dichlorofluorescin acetate (DCFA, Sigma Chemical) or 5 μg/mL dichlorofluorescin acetate for 10 minutes at 37° C. Cultures were treated with trypsin for 5 minutes to form a single cell suspension, and analyzed using a flow cytometer (Becton-Dickenson) within 20 minutes.

Figure 4:
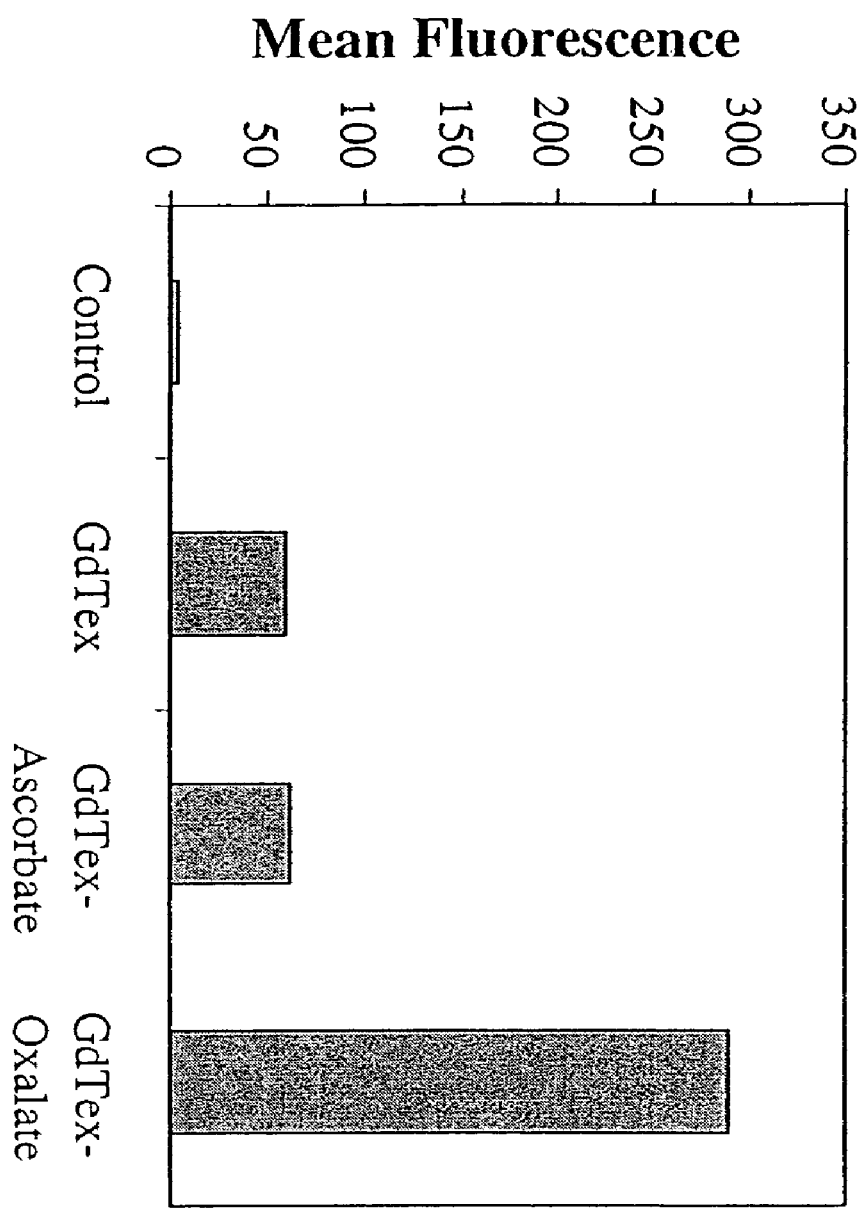
FIG. 4 depicts uptake in A549 cells as measured using flow cytometry (see Example 8).
Figure 5:
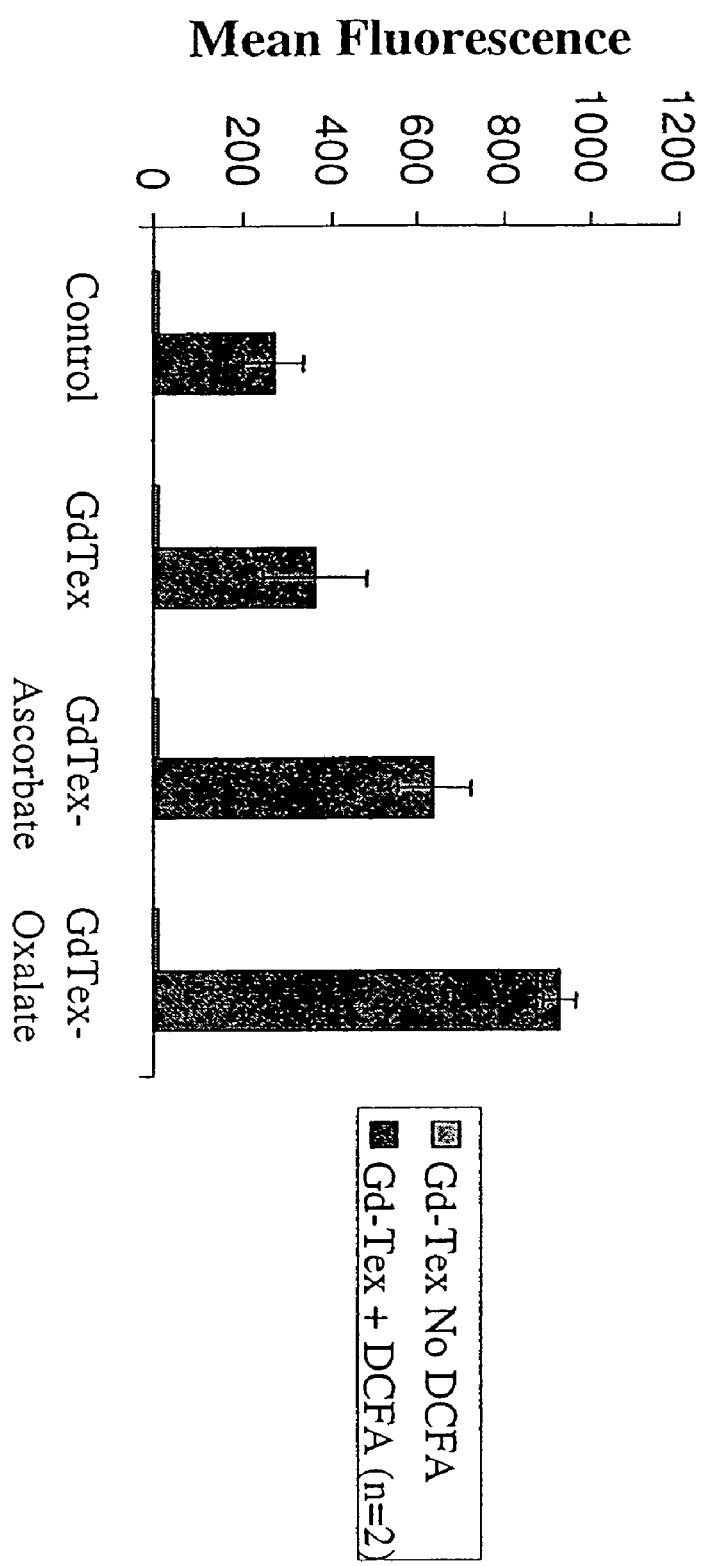
FIG. 5 depicts oxidation in A549 cells as measured using flow cytometry (see Example 8).

The results are shown in FIGS. 4 and 5. The fluorescence in channel FL3 (>650 nm, FIG. 4) corresponds to fluorescence derived from Gd-Tex. The Gd-Tex-oxalate complex is relatively non-fluorescent (as compared to Gd-Tex) and so there appears to be similar uptake of Gd-Tex in the Gd-Tex and Gd-Tex plus ascorbate groups. However, the enhanced fluorescence seen in the culture treated with Gd-Tex oxalate complex indicates that dissociation back to free (i.e., fluorescent) Gd-Tex can occur within the cell or that there is sufficient uptake of this species to give rise to the greater fluorescence signal despite its lower fluorescent quantum yield. The fluorescence in channel FL1 (530+/−15 nm, FIG. 5) corresponds to fluorescence from dichlorofluorescin, produced upon intracellular oxidation of DCFA. In this figure, enhanced uptake in groups treated with Gd-Tex in the presence of ascorbate, and pre-formed Gd-Tex oxalate complex, is seen indirectly via the greater oxidative stress produced in these groups, relative to cultures treated with Gd-Tex alone.

EXAMPLE 9

In Vivo Rabbit Study

TABLE 1

Experimental Regimens

| Groups | Test Article 1 | Test Article 2 |
|---|---|---|
| 1* | 0.9% NaCl | 5% Mannitol (simultaneous) |
| 2* | 0.9% NaCl | MGd 10 mg/kg (simultaneous) |
| 3* | Ascorbate 500 mg/kg | 5% Mannitol (simultaneous) |
| 4* | Ascorbate 500 mg/kg | MGd 10 mg/kg (simultaneous) |
| 5 | Ascorbate 500 mg/kg, first | MGd 10 mg/kg, 4 hours later |
| 6 | MGd 10 mg/kg, first | Ascorbate 500 mg/kg, 4 hours later |

Notes:
MGd: 2.5 mg/ml; Sodium Ascorbate: 250 mg/ml, diluted in same amount of 0.9% NaCl for injection.
*Injected simultaneously through a different ear vein. Injected slowly (4 to 5 minutes for each injection) flushing with 0.9% NaCl 1 to 2 ml after each injection. Before surgery, all rabbits were fed a 2% cholesterol diet (Harlan Tekland, Lot 215496) for a total of six weeks (two weeks before the surgery and four weeks after); and supplied aspirin water (1.4 g per 20 liters) at least 1 day prior to the surgery until 10 to 14 days post iliac denudation.

Surgery

Rabbits were injected subcutaneously with ketamine/diazepam or ketamine/xylazine cocktail (ketamine 45 mg/kg; diazepam 2.5 mg/kg and xylazine 5 mg/kg) as anesthesia, and then clipped with Oster size 40 clippers to expose the lower abdomen and rear legs. Anesthesia was maintained by isofluorane inhalation, usually 2% to 3% isoflurane (isofluorane machine from Fraser Lake, equipped with Fluotec 3 vaporizer calibrated 8/1/01 with a mask to a surgical plane of anesthesia-Plane 3). A pain/reflex toe pinch method was used to monitor the level of anesthesia. The eyes were coated with artificial tears. The iliac denudation was an aseptic surgery. Betadine (Betadine brand surgical scrub) providone/iodine 7.5% and 70% alcohol were used to swab the surgical area repetitively 3 times. A bilateral femoral arteriotomy was made distal to the inguinal ligament. Lidocaine (2%) was used topically to prevent nerve spasms. A No.3 French Fogarty balloon (Baxter Fogarty Arterial Embolectomy catheter) was inserted retrograde 20 cm via the iliac incision. The balloon was inflated with up to 0.5 ml air and pulled back 18 cm toward the femoral artery. Then the balloon was deflated; inserted, inflated and pulled back again repetitively 3 times. The femoral artery was ligated and the same procedure was repeated on the contra-lateral femoral artery. The underlying muscle in the incision area was sutured with 3-0 absorbable chromic gut, and skin was sutured with 3-0 monofilament nylon. The rabbits lay on a heating pad (37° C.) during the whole surgical procedure. The sutures were removed 7 to 10 days after surgery. Buprenex (0.03 mg/kg, intramuscularly) and penicillin G benzathine/procaine (75,000 IU, subcutaneous) were injected post surgery for relieving pain and preventing infection. Animals were observed intensively until completely awake and were returned to their cages.

Post Surgery

After continuing on a 2% cholesterol diet for another 4 weeks post surgery, all rabbits were randomized into 6 groups (7 animals per group). Either drug or vehicle was injected intravenously via ear marginal vein (Table 1). All animals were returned to normal rabbit chow for 4 weeks after injection.

Euthanasia and Sample Collection

Serum (for C-reactive protein measurement at Ani Lytics, Inc.) was collected through the ear artery. Rabbits were sacrificed via intravenous injection of Euthasol (390 mg/ml pentobarbital, 125 mg/kg). The abdominal aorta and iliac arteries were perfused at 25 ml per minute with 120 ml saline and 240 ml 10% buffered formalin before being harvested. A 4 cm long denuded section of each iliac artery was marked with suture string as an indicator of the segment to be further examined by histology. The arterial segments from 1 cm above bifurcation of iliac arteries to 6 cm below the bifurcation were also expanded and fixed in 10% buffered formalin for assessment of intima/media ratio (H & E and Van Giessen stain) and macrophage burden (RAM 11 stain performed at IDEXX, Sacramento, Calif.). The rest of the aorta was collected for evaluation of surface atherosclerotic lesions (Sudan IV stain) by planimetry (PLANIX 7, Tamaya digital planimeter, Japan), and divided into two halves, the top and bottom sections. The percentage surface lesion coverage was defined as the sum of the total lesion area divided by the whole aortic area and then multiplied by 100. Slide reading was done blindly, averaged by at least two persons and repeated until the resulting difference between the two readers was within 10%.

EXAMPLE 10

Flow Cytometry

THP-1: PMA Transformed adherent THP-1macrophages were plated in 5 ml RPMI +10% dialysed FBS ($1\times10^6$ cells per plate). Media was removed and replaced with 5 ml RPMI+sterile water (control) or 5 ml RPMI+50 µM GdTex.

SMC: Human primary cells: Human Coronary Artery Smooth Muscle Cells (HCASMC) Clonetics were plated in 5 ml semi-defined EGM-2 ($1\times10^6$ cells per plate) and allowed to adhere overnight. Media was removed and replaced with 5 ml EGM-2+sterile water (control) or 5 ml EGM-2+50 µM GdTex.

EC: Human primary cells: Human Coronary Artery Endothelial Cells (HCAEC) Clonetics were plated in 5 ml semi-defined EGM-2 ($1\times10^6$ cells per plate) and allowed to adhere overnight. Media was removed and replaced with 5 ml EGM-2+sterile water (control) or 5 ml EGM-2+50 µM GdTex.

Plates were incubated for 24 hours at 37° C., washed ×2 in 5 ml Dulbecco's PBS, (Ca/Mg free) and trypsinised for 5 minutes. A reaction was stopped with 10% FBS in HBSS. Cells were centrifuged for 5 minutes and resuspended in 1 ml HBSS. Tubes were labeled and fluorescence read in the FL3 channel (>650 nm, texaphyrin). All conditions were performed in triplicate.

EXAMPLE 11

DNA Synthesis, Cell Proliferation and Cell Death

DNA synthesis in the cells was determined by [$^3$H]-Thymidine incorporation assay. Cells (30,000 per well) were seeded into 24-well plates in serum-rich growth media, allowed to grow for 2 days to reach to near confluence, and growth-arrested in serum-free media for 18 to 24 hours to synchronize most cells at G0/G1. Cells were subjected to the treatment for 24 hours, and incubated with 1 µCi per well of [$^3$H]-thymidine (ICN Biomedicals, Irvine, Calif., USA) during the last 4 to 6 hours of the stimulation. The cells were washed 3 times with ice-cold Dulbecco's PBS, incubated with ice-cold 0.2 N $HClO_4$ (1 ml per well) on ice for 30 minutes, washed (0.5 ml per well, 3 times) with 0.2 N $HClO_4$, incubated with 0.5 ml per well of 0.2 N NaOH in 37° C. for 1 hour, and neutralized with 0.2 ml per well of 6% acetic acid. Contents of the wells were transferred into scintillation vials with 3 ml Scintillation Liquid Instagel (BIO-RAD, Australia) and counted for 2 minutes per vial in a β-counter.

Cells (20,000 per well) were seeded into 24-well plates in serum-rich growth media, allowed to grow for 24 hours to reach ~70% confluence, and subjected to the treatment. The cells floating in media (dead cells), or cells attaching the plates harvested by 0.5% trypsin digestion, were counted by an automatic cell counter (S.ST.II/ZM, Coulter Electronics Ltd., England).

Utility, Testing and Administration

General Utility

The compounds of the present invention are effective in the treatment of conditions known to respond to metallotexaphyrin therapy, including diseases characterized by neoplastic tissue, (e.g. the cancers sarcoma, lymphoma, leukemia, carcinoma, brain metastases, glioma, glioblastoma, cancer of the prostate, melanoma, and the like), cardiovascular diseases (e.g., atherosclerosis, intimal hyperplasia and restenosis) and other activated macrophage-related disorders including autoimmune diseases (e.g., rheumatoid arthritis, Sjogrens, scleroderma, systemic lupus erythematosus, non-specific vasculitis, Kawasaki's disease, psoriasis, Type I diabetes, pemphigus vulgaris, multiple sclerosis), granulomatous diseases (e.g., tuberculosis, sarcoidosis, lymphomatoid granulomatosis, Wegener's granulomatosis), inflammatory diseases (e.g., inflammatory lung diseases such as interstitial pneumonitis and asthma, inflammatory bowel disease such as Crohn's disease, and inflammatory arthritis), in transplant rejection (e.g., in heart/lung transplants) and in ophthalmic diseases that result from undesired neovascularization, in particular age-related macular degeneration.

Testing

Activity testing is conducted as described in those patents and patent applications incorporated by reference above, and in the following references, and by modifications thereof. The compounds of the invention have been shown to have various in vitro and in vivo activity. See, for example, Young et al., Methods for Cancer Chemosensitization, and U.S. Pat. No. 5,776,925.

Pharmaceutical Compositions

The compounds of the present invention are usually administered in the form of pharmaceutical compositions. This invention therefore provides pharmaceutical compositions that contain, as the active ingredient, one or more of the compounds (coordination polymer) of the present invention, or a pharmaceutically acceptable salt thereof, and one or more pharmaceutically acceptable excipients, carriers, including inert solid diluents and fillers, diluents, including sterile aqueous solution and various organic solvents, permeation enhancers, solubilizers and adjuvants. The compounds may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of the invention may be administered in either single or multiple doses by any of the accepted modes of administration of agents having similar utilities, for example as described in those patents and patent applications incorporated by reference above, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer, with parenteral and intra-arterial administration being preferred, and intra-arterial being more preferred.

One preferred mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present. invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parables, chlorobutanol, phenol, sorbic acid, thimerosal, and the like.

Sterile inject able solutions are prepared by incorporating the active compounds in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile inject able solutions, the preferred methods of preparation are vacuum-drying and freeze-drying techniques which yield a powder of the active ingredient plus any additional desired ingredient from a previously sterile-filtered solution thereof.

Compounds of the invention may be impregnated into a stent by diffusion, for example, or coated onto the stent such as in a gel form, for example, using procedures known to one of skill in the art in light of the present disclosure.

Oral administration is another route for administration of the compounds of this invention. Preferred is oral administration via capsule or enteric coated tablets, or the like, which prevent degradation of the compounds of the invention in the stomach. In making the pharmaceutical compositions that include at least one compound of the invention, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile inject able solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another preferred formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The active compound is effective over a wide dosage range and is generally administered in a pharmaceutically effective amount. Preferably, for oral administration, each dosage unit contains from 10 mg to 2 g of an compound of the invention, and for parenteral administration, preferably from 10 to 700 mg of an compound of the invention, preferably about 350 mg. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of an compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Dosages

The specific dose will vary depending on the particular compound of the invention chosen, the dosing regimen to be followed, and the particular therapeutic energy or agent with which it is administered, employing dosages within the range of about 0.01 mg/kg/treatment up to about 100 mg/kg/treatment, preferably about 0.1 mg/kg/treatment to about 50 mg/kg/treatment. It will be appreciated by one skilled in the art, however, that there are specific differences in the most effective dosimetry depending on the apical ligands chosen, because of the wide range of properties available, such as solubilities, lipophilicity properties, lower toxicity, and improved stability.

Administration for Photodynamic Therapy

By way of example, a compound of Formula I, having lutetium as a metal in the Texaphyrin, may be administered in solution, optionally in 5% mannitol USP. Dosages of about 1.0–2.0 mg/kg to about 4.0–7.0 mg/kg, preferably 3.0 mg/kg, are employed, although in some cases a maximum tolerated dose may be higher, for example about 5 mg/kg. The Texaphyrin is administered by intravenous injection, followed by a waiting period of from as short a time as several minutes or about 3 hours to as long as about 72 or 96 hours (depending on the treatment being effected) to facilitate intracellular uptake and clearance from the plasma and extracellular matrix prior to the administration of photoirradiation.

Dose levels for certain uses may range from about 0.05 mg/kg to about 20 mg/kg administered in single or multiple doses (e.g. before each fraction of radiation). The lower dosage range would be preferred for intra-arterial injection or for impregnated stents.

The optimum length of time following administration of an compound of the invention until light treatment can vary depending on the mode of administration, the form of administration, and the type of target tissue. Typically, the compound of the invention persists for a period of minutes to hours, depending on the compound of the invention, the formulation, the dose, the infusion rate, as well as the type of tissue and tissue size.

When employing photodynamic therapy, a target area is treated with light at about 780±16.5 nm. After the photosensitizing compound of the invention has been administered, the tissue being treated is photo irradiated at a wavelength similar to the absorbance of the compound of the invention, usually either about 440–540 nm or about 740–840 nm, more preferably about 490–540 nm or about 750–800 nm, or most preferably about 450–500 nm or about 765–780 nm. The light source may be a laser, a light-emitting diode, or filtered light from, for example, a xenon lamp; and the light may be administered topically, endoscopically, or interstitially (via, e.g., a fiber optic probe), or intra arterially. Preferably, the light is administered using a slit-lamp delivery system. The fluence and irradiance during the photo irradiating treatment can vary depending on type of tissue, depth of target tissue, and the amount of overlying fluid or blood. For example, a total light energy of about 100 $J/cm^2$ can be delivered at a power of 200 mW to 250 mW, depending upon the target tissue.

Compounds of the invention may be administered before, at the same time, or after administration of one or more chemotherapeutic drugs. The compound of the invention may be administered as a single dose, or it may be administered as two or more doses separated by an interval of time. The compound of the invention may be administered concurrently with, or from about one minute to about 12 hours following, administration of a chemotherapeutic drug, preferably from about 5 min to about 5 hr, more preferably about 4 to 5 hr. The dosing protocol may be repeated, from one to three times, for example. A time frame that has been successful in vivo is administration of a compound of the invention about 5 min and about 5 hr after administration of a chemotherapeutic agent, with the protocol being performed once per week for three weeks. Administration may be intra-arterial injection, intravenous, intraperitoneal, intramuscular, subcutaneous, oral, topical, or via a device such as a stent, for example, with parenteral and intra-arterial administration being preferred, and intra-arterial being more preferred.

Administering a compound of the invention and a chemotherapeutic drug to the subject may be prior to, concurrent with, or following vascular intervention. The method may begin at a time roughly accompanying a vascular intervention, such as an angioplastic procedure, for example. Multiple or single treatments prior to, at the time of, or subsequent to the procedure may be used. "Roughly accompanying a vascular intervention" refers to a time period within the ambit of the effects of the vascular intervention. Typically, an initial dose of an compound of the invention and chemotherapeutic drug will be within 6–12 hours of the vascular intervention, preferably within 6 hours thereafter. Follow-up dosages may be made at weekly, biweekly, or monthly intervals. Design of particular protocols depends on the individual subject, the condition of the subject, the design of dosage levels, and the judgment of the attending practitioner.

Administration for Radiation Sensitization

Compounds of the invention where the metal is gadolinium are typically administered in a solution containing 2 mM optionally in 5% mannitol USP/water (sterile and non-pyrogenic solution). Dosages of 0.1 mg/kg up to as high as about 29.0 mg/kg have been delivered, preferably about 3.0 to about 15.0 mg/kg (for volume of about 90 to 450 mL) may be employed, optionally with pre-medication using anti-emetics when dosing above about 6.0 mg/kg. The compound is administered via intravenous injection over about a 5 to 10 minute period, followed by a waiting period of about 2 to 5 hours to facilitate intracellular uptake and clearance from the plasma and extracellular matrix prior to the administration of radiation.

When employing whole brain radiation therapy, a course of 30 Gy in ten (10) fractions of radiation may be administered over consecutive days excluding weekends and holidays. In the treatment of brain metastases, whole brain megavolt radiation therapy is delivered with $^{60}Co$ teletherapy or a $\geq 4$ MV linear accelerator with isocenter distances of at least 80 cm, using isocentric techniques, opposed lateral fields and exclusion of the eyes. A minimum dose rate at the midplane in the brain on the central axis is about 0.5 Gy/minute.

Compounds of the invention used as radiation sensitizers may be administered before, or at the same time as, or after administration of the ionizing radiation. The compound of the invention may be administered as a single dose, as an infusion, or it may be administered as two or more doses separated by an interval of time. Where the compound of the invention is administered as two or more doses, the time interval between the compound of the invention administrations may be from about one minute to a number of days, preferably from about 5 min to about 1 day, more preferably about 4 to 5 hr. The dosing protocol may be repeated, from one to ten or more times, for example. Dose levels for radiation sensitization may range from about 0.05 mg/kg to about 20 mg/kg administered in single or multiple doses (e.g. before each fraction of radiation). The lower dosage range would be preferred for intra-arterial injection or for impregnated stents.

Administration may be intra-arterial injection, intravenous, intraperitoneal, intramuscular, subcutaneous, oral, topical, or via an impregnated or coated device such as a stent, for example, or an artery-inserted cylindrical polymer, with intravenous and intra-arterial administration being preferred, and intra-arterial being more preferred. In one aspect of the invention, a patient having restenosis or at risk for restenosis is administered a dose of compound of the invention at intervals with each dose of radiation.

Administering a compound of the invention to the subject may be prior to, concurrent with, or following vascular intervention, and the intervention is followed by radiation. The method may begin prior to, such as about 24–48 hours prior to, or at a time roughly accompanying vascular intervention, for example. Multiple or single treatments prior to, at the time of, or subsequent to the procedure may be used. "Roughly accompanying the vascular intervention" refers to a time period within the ambit of the effects of the vascular intervention. Typically, an initial dose of compound of the invention and radiation will be within 1–24 hours of the vascular intervention, preferably within about 5–24 hours thereafter. Follow-up dosages may be made at weekly, biweekly, or monthly intervals. Design of particular protocols depends on the individual subject, the condition of the subject, the design of dosage levels, and the judgment of the attending practitioner.

Administration for Sonodynamic Therapy

The use of texaphyrins in sonodynamic therapy is described in U.S. patent application Ser. No. 09/111,148, which was converted to U.S. Provisional Application Ser. No. 60/155,256, from which a continuation was filed on Jan. 5, 2001, having U.S. patent application Ser. No. 09/755,824, now abandoned, which is incorporated herein by reference. Texaphyrin is administered before administration of the ultrasound. The Texaphyrin may be administered as a single dose, or it may be administered as two or more doses separated by an interval of time. Parenteral administration is typical, including by intravenous and interarterial injection. Other common routes of administration can also be employed.

Ultrasound is generated by a focused array transducer driven by a power amplifier. The transducer can vary in diameter and spherical curvature to allow for variation of the focus of the ultrasonic output. Commercially available therapeutic ultrasound devices may be employed in the practice of the invention. The duration and wave frequency, including the type of wave employed may vary, and the preferred duration of treatment will vary from case to case within the judgment of the treating physician. Both progressive wave mode patterns and standing wave patterns have been successful in producing cavitation of diseased tissue. When using progressive waves, the second harmonic can advantageously be superimposed onto the fundamental wave.

Preferred types of ultrasound employed in the present invention are ultrasound of low intensity, non-thermal ultrasound, i.e., ultrasound generated within the wavelengths of about 0.1 MHz and 5.0 MHz and at intensities between about 3.0 and 5.0 W/cm$^2$.

Utility

Pharmaceutical Formulations

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50 to 60 C and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 4

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 5

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 6

Capsules are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 7

An injectable preparation buffered to a pH of 7.4 is prepared having the following composition:

| Ingredients | Amount |
| --- | --- |
| Active Ingredient | 0.2 g |
| Sodium Phosphate Buffer Solution (0.8 M) | 10.0 ml |
| DMSO | 1.0 ml |
| WFI | q.s. to 100 ml |

FORMULATION EXAMPLE 8

An injectable formulation is prepared having the following composition:

| Ingredients | Amount (w/v %) |
| --- | --- |
| Motexafin gadolinium | 0.23% |
| Motexafin lutetium | 0.20% |
| Mannitol (USP) | 5.0% |
| Acetic Acid (5%) | adjust to pH 5.4 |
| Sterile WFI (USP) | q.s. to 100% |

The formulation is filled into a glass vials, which are then purged with nitrogen to exclude oxygen from the head space and then sealed.

It may be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa., 17th ed. (1985).

ABBREVIATIONS

In the examples the following abbreviations have the following meanings. If an abbreviation is not defined, it has its generally accepted meaning.

| | |
| --- | --- |
| Cd-Tex = | compound of formula A where M is $Cd^{2+}$ |
| Co-Tex = | compound of formula A where M is $Co^{2+}$ |
| Dy-Tex = | compound of formula A where M is $Dy^{3+}$ |
| Eu-Tex = | compound of formula A where M is $Eu^{3+}$ |
| Gd-Tex = | motexafin gadolinium (formula A where M is $Gd^{3+}$) |

-continued

| | |
|---|---|
| HPLC = | high performance liquid chromatography |
| Lu-Tex = | motexafin lutetium (formula A where M is $Lu^{3+}$) |
| mg = | milligram |
| mL = | milliliter |
| mm = | millimeter |
| mM = | millimolar |
| MnTex = | compound of formula II where M is $Mn^{2+}$ |
| mmol = | millimoles |
| nm = | nanometer |
| psi = | pounds per square inch |
| SmTex = | compound of formula A where M is $Sm^{3+}$ |
| YTex = | compound of formula A where M is $Y^{3+}$ |
| μL = | micro liter |
| μM = | micro molar |
| HepG2 = | a type of hepatocyte (liver) cancer cell |

What is claimed is:

1. A method for treating atherosclerotic inflammation in a mammal, said process comprising administering to the mammal:
   (a) a reducing agent; and
   (b) a compound of Formula I

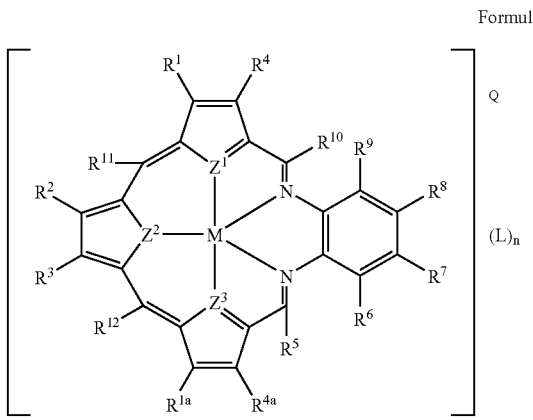

Formula I its hydrate, pharmaceutically acceptable salt or prodrug form thereof, wherein:
M represents H or a metal cation;
Q represents an integer of from about −5 to about +5;
L represents a charge balancing species;
n represents an integer of from 0 to +5;
$Z^1$, $Z^2$ and $Z^3$ independently represent N, O, CH or S;
$R^1$, $R^{1a}$, $R^2$, $R^3$, $R^4$, $R^{4a}$, $R^7$, and $R^8$ are independently selected from acyl, acyloxy, optionally substituted alkenyl, optionally substituted alkoxy, optionally substituted alkyl, optionally substituted alkynyl, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydrogen, hydroxyl, nitro, optionally substituted azo, $S—R^{31}$, $SO—R^{31}$, $SO_2—R^{31}$, and the moiety X—Y;
$R^6$ and $R^9$ are independently selected from acyl, acyloxy, optionally substituted alkenyl, optionally substituted alkoxy, optionally substituted alkyl, optionally substituted alkynyl, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, optionally substituted cycloalkenyl, fluoro, chloro, bromo, optionally substituted heteroaryl, optionally substituted heteroaryloxy, optionally substituted heterocyclyl, optionally substituted heterocyclooxy, hydrogen, hydroxyl, nitro, optionally substituted azo, sulfanyl, sulfinyl, sulfonyl, and the moiety X—Y;
$R^5$, $R^{10}$, $R^{11}$ and $R^{12}$ are independently selected from acyl, optionally substituted alkoxy, optionally substituted alkyl, optionally substituted aryl, halo, hydrogen, hydroxy, optionally substituted cycloalkyl, optionally substituted cycloalkenyl, optionally substituted heteroaryl, and optionally substituted heterocyclyl;
X is a covalent bond or a linker;
Y is a catalytic group, a chemotherapeutic agent or a site-directing group;
$R^{31}$ represents acyl, optionally substituted alkenyl, optionally substituted alky, optionally substituted alkoxy, optionally substituted alkoxycarbonyl, optionally substituted alkynyl, optionally substituted aminocarbonyl, optionally substituted aryl, carboxy, optionally substituted cycloalkyl, optionally substituted heteroaryl, or optionally substituted heterocyclyl.

2. A process of claim 1 wherein the compound of Formula I is represented by

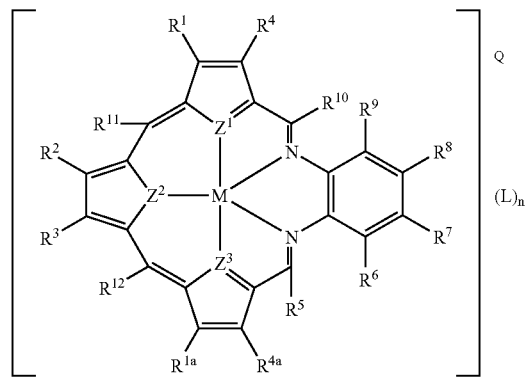

its hydrate, pharmaceutically acceptable salt or prodrug form thereof, wherein:
M represents a metal cation selected from Gd(III) and Lu(III);
Q represents an integer of 2;
L represents a charge balancing species selected from OAc, $NO_2$, Cl, and $PO_4$;
n represents an integer of 2;
$Z^1$, $Z^2$ and $Z^3$ independently represent N;
$R^1$ and $R^{1a}$ independently represent $(CH_2)_3OH$;
$R^2$ and $R^3$ independently represent $C_2H_5$;
$R^4$ and $R^{4a}$ independently represent $CH_3$;
$R^7$ and $R^8$ independently represent $O—(CH_2—CH_2—O)_3—CH_3$; and
$R^5$, $R^6$, $R^9$, $R^{10}$, $R^{11}$ and $R^{12}$ independently represent H.

3. A process of claim 2 wherein the reducing agent and the compound of Formula I

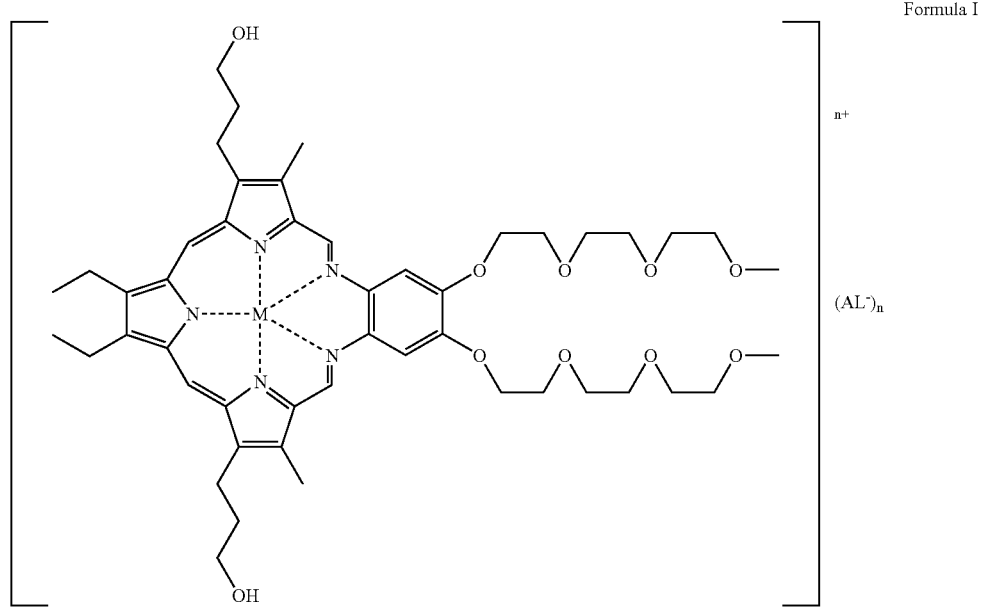

Formula I wherein

M independently at each occurrence represents Gd(III), Lu(III), Eu(III), Tb(III), Dy(III), Ho(III), Er(III), Tm(III), Yb(III), or Y(III); and n represents an integer from 1 to 3;

are intravenously administered to the host.

4. A process of claim 3 wherein the reducing agent is selected from ascorbic acid, dehydroascorbate, dihydrolipoate, NADH, folate, glyoxal, glyoxalate, oxamate, dimethyloxalate, oxamide, NADPH, glutathione, nacetylcystein and pyruvate.

5. A process of claim 4 wherein the reducing agent is administered at least about 30 minutes before administering a compound of Formula I.

6. A process of claim 5 wherein the reducing agent and a compound of Formula I are administered simultaneously to the host.

7. A process of claim 6 wherein the host is administered a mixture of the reducing agent and a compound Formula I.

8. A process of claim 7 wherein the host is administered the reducing agent after the administration of a compound of Formula I.

* * * * *